(12) United States Patent
Beyar et al.

(10) Patent No.: US 8,439,890 B2
(45) Date of Patent: May 14, 2013

(54) MATERIAL DELIVERY SYSTEM

(75) Inventors: Mordechay Beyar, Caesarea (IL); Oren Globerman, Kfar-Shemaryahu (IL); Rami Keller, Tel-Aviv (IL)

(73) Assignee: By-pass, Inc., Orangeburg, NY (US)

( * ) Notice: Subject to any disclaimer, the term of this patent is extended or adjusted under 35 U.S.C. 154(b) by 0 days.

(21) Appl. No.: 13/304,756

(22) Filed: Nov. 28, 2011

(65) Prior Publication Data

US 2012/0071715 A1    Mar. 22, 2012

Related U.S. Application Data

(60) Division of application No. 11/335,317, filed on Jan. 19, 2006, which is a continuation-in-part of application No. PCT/IL2005/000749, filed on Jul. 14, 2005, application No. 13/304,756, which is a division of application No. 11/632,476, filed as application No. PCT/IL2005/000749 on Jul. 14, 2005.

(60) Provisional application No. 60/587,335, filed on Jul. 14, 2004, provisional application No. 60/599,884, filed on Aug. 10, 2004, provisional application No. 60/603,262, filed on Aug. 23, 2004, provisional application No. 60/675,477, filed on Apr. 28, 2005.

(51) Int. Cl.
*A61M 31/00* (2006.01)
*A61M 29/00* (2006.01)

(52) U.S. Cl.
USPC ........ 604/507; 604/500; 604/509; 604/98.01; 604/101.02; 606/192

(58) Field of Classification Search ............... 604/93.01, 604/94.01, 95.01, 95.02, 95.03, 96.01, 97.01, 604/98.01, 99.01, 101.02, 103.01, 103.02, 604/915, 500, 507, 509; 606/192, 195
See application file for complete search history.

(56) References Cited

U.S. PATENT DOCUMENTS

| 4,793,349 A | 12/1988 | Weinrib |
| 4,990,134 A | 2/1991 | Auth |
| 4,994,033 A * | 2/1991 | Shockey et al. .......... 604/101.02 |
| 5,049,132 A * | 9/1991 | Shaffer et al. ............ 604/101.02 |
| 5,053,041 A | 10/1991 | Ansari et al. |
| 5,087,244 A | 2/1992 | Wolinsky et al. |
| 5,098,381 A | 3/1992 | Schneider |

(Continued)

FOREIGN PATENT DOCUMENTS

| DE | 4225553 | 5/1994 |
| EP | 0712615 | 5/1996 |

(Continued)

OTHER PUBLICATIONS

Official Action Dated Mar. 27, 2012 From the US Patent and Trademark Office Re. U.S. Appl. No. 11/335,317.

(Continued)

*Primary Examiner* — Quynh-Nhu H Vu

(57) ABSTRACT

A method for injecting a therapeutic agent into a target tissue, the method comprising: (a) providing an expandable member; (b) positioning said expandable member in proximity to the target tissue; (c) Introducing the therapeutic agent into the expandable member until a desired pressure is achieved; and (d) creating a plurality of small apertures in the expandable member.

38 Claims, 20 Drawing Sheets

U.S. PATENT DOCUMENTS

| | | | |
|---|---|---|---|
| 5,180,366 A | 1/1993 | Woods | |
| 5,213,576 A | 5/1993 | Abiuso et al. | |
| 5,232,444 A | 8/1993 | Just et al. | |
| 5,306,250 A | 4/1994 | March et al. | |
| 5,314,407 A | 5/1994 | Auth et al. | |
| 5,336,178 A | 8/1994 | Kaplan et al. | |
| 5,358,487 A * | 10/1994 | Miller | 604/103.11 |
| 5,364,356 A | 11/1994 | Hofling | |
| 5,364,393 A | 11/1994 | Auth et al. | |
| 5,421,826 A | 6/1995 | Crocker et al. | |
| 5,447,497 A * | 9/1995 | Sogard et al. | 604/101.02 |
| 5,611,775 A * | 3/1997 | Machold et al. | 604/509 |
| 5,614,502 A * | 3/1997 | Flotte et al. | 514/34 |
| 5,704,911 A | 1/1998 | Parsons | |
| 5,730,723 A | 3/1998 | Castellano et al. | |
| 5,746,716 A | 5/1998 | Vigil et al. | |
| 5,814,016 A | 9/1998 | Valley et al. | |
| 5,817,144 A * | 10/1998 | Gregory | 607/89 |
| 5,836,940 A * | 11/1998 | Gregory | 606/15 |
| 5,858,400 A | 1/1999 | Williams | |
| 5,891,085 A | 4/1999 | Lilley et al. | |
| 6,027,514 A | 2/2000 | Stine et al. | |
| 6,036,700 A | 3/2000 | Stefanchik et al. | |
| 6,280,411 B1 * | 8/2001 | Lennox | 604/103.05 |
| 6,280,414 B1 | 8/2001 | Shah et al. | |
| 6,299,622 B1 | 10/2001 | Snow et al. | |
| 6,344,027 B1 | 2/2002 | Goll | |
| 6,364,856 B1 | 4/2002 | Ding et al. | |
| 6,447,525 B2 | 9/2002 | Follmer et al. | |
| 6,544,223 B1 | 4/2003 | Kokish | |
| 6,623,452 B2 | 9/2003 | Chien et al. | |
| 6,623,496 B2 | 9/2003 | Snow et al. | |
| 6,629,953 B1 | 10/2003 | Boyd | |
| 6,638,233 B2 | 10/2003 | Corvi et al. | |
| 6,699,231 B1 | 3/2004 | Sterman et al. | |
| 6,716,190 B1 | 4/2004 | Glines et al. | |
| 6,733,474 B2 * | 5/2004 | Kusleika | 604/103.01 |
| 6,964,649 B2 | 11/2005 | Goll | |
| 6,997,934 B2 | 2/2006 | Snow et al. | |
| 2001/0035456 A1 | 11/2001 | Lennox | |
| 2002/0107504 A1 | 8/2002 | Gordon | |
| 2002/0115982 A1 | 8/2002 | Barbut et al. | |
| 2003/0060876 A1 | 3/2003 | Kilemnik et al. | |
| 2004/0073169 A1 | 4/2004 | Amisar et al. | |
| 2004/0181252 A1 | 9/2004 | Boyle et al. | |
| 2004/0236308 A1 * | 11/2004 | Herweck et al. | 604/509 |
| 2004/0260239 A1 | 12/2004 | Kusleika | |
| 2005/0288632 A1 | 12/2005 | Willard | |
| 2006/0184118 A1 | 8/2006 | Hjertman | |
| 2006/0190022 A1 | 8/2006 | Beyar et al. | |
| 2007/0299392 A1 | 12/2007 | Beyar et al. | |
| 2008/0140001 A1 | 6/2008 | Globerman et al. | |
| 2010/0191215 A1 | 7/2010 | Globerman et al. | |

FOREIGN PATENT DOCUMENTS

| | | |
|---|---|---|
| EP | 0835673 | 4/1998 |
| GB | 2426457 | 11/2006 |
| JP | 2000-070367 | 3/2000 |
| WO | WO 02/43796 | 6/2002 |
| WO | WO 2005/027750 | 3/2005 |
| WO | WO 2006/006169 | 1/2006 |
| WO | WO 2006/114783 | 11/2006 |
| WO | WO 2008/072228 | 6/2008 |
| WO | WO 2008/152639 | 12/2008 |

OTHER PUBLICATIONS

Communication Pursuant to Article 94(3) EPC Dated Apr. 19, 2011 From the European Patent Office Re.: Application No. 05759764.3.

International Preliminary Report on Patentability Dated Nov. 8, 2007 From the International Bureau of WIPO Re.: Application No. PCT/IL2006/000087.

International Preliminary Report on Patentability Dated Jan. 25, 2007 From the International Bureau of WIPO Re.: Application No. PCT/IL2005/000749.

International Preliminary Report on Patentability Dated Jan. 28, 2010 From the International Bureau of WIPO Re.: Application No. PCT/IL2008/000802.

International Search Report Dated Nov. 5, 2008 From the International Searching Authority Re.: Application No. PCT/IL08/00802.

Interview Summary Dated Feb. 16, 2011 From the US Patent and Trademark Office Re. U.S. Appl. No. 11/335,317.

Interview Summary Dated Feb. 16, 2011 From the US Patent and Trademark Office Re.: U.S. Appl. No. 11/335,317.

Office Action Dated Feb. 27, 2009 From the State Intellectual Property Office Re.: Application No. 200580030380.2 and Its Translation Into English.

Office Action Dated Aug. 31, 2009 From the Israeli Patent Office Re.: Application No. 180661 and Its Translation Into English.

Official Action Dated Aug. 4, 2010 From the US Patent and Trademark Office Re.: U.S. Appl. No. 11/609,451.

Official Action Dated Oct. 5, 2009 From the US Patent and Trademark Office Re.: U.S. Appl. No. 11/609,451.

Official Action Dated Apr. 6, 2010 From the US Patent and Trademark Office Re.: U.S. Appl. No. 11/335,317.

Official Action Dated Jul. 10, 2008 From the US Patent and Trademark Office Re.: U.S. Appl. No. 11/335,317.

Official Action Dated Dec. 13, 2007 From the US Patent and Trademark Office Re.: U.S. Appl. No. 11/335,317.

Official Action Dated Oct. 13, 2010 From the US Patent and Trademark Office Re.: U.S. Appl. No. 11/335,317.

Official Action Dated May 14, 2010 From the US Patent and Trademark Office Re.: U.S. Appl. No. 11/632,476.

Official Action Dated Apr. 15, 2009 From the US Patent and Trademark Office Re.: U.S. Appl. No. 11/632,476.

Official Action Dated May 18, 2009 From the US Patent and Trademark Office Re.: U.S. Appl. No. 11/609,451.

Official Action Dated May 18, 2011 From the US Patent and Trademark Office Re. U.S. Appl. No. 11/335,317.

Official Action Dated Aug. 19, 2009 From the US Patent and Trademark Office Re.: U.S. Appl. No. 11/632,476.

Official Action Dated Feb. 26, 2009 From the US Patent and Trademark Office Re.: U.S. Appl. No. 11/335,317.

Official Action Dated Oct. 27, 2009 From the US Patent and Trademark Office Re.: U.S. Appl. No. 11/335,317.

Proceedings Further With the European Patent Application Pursuant to Rule 70(2) EPC Dated Jan. 4, 2010 From the European Patent Office Re.: Application No. 05759764.3.

Response Dated Apr. 1, 2010 to Official Action of Oct. 5, 2009 From the US Patent and Trademark Office Re.: U.S. Appl. No. 11/609,451.

Response Dated Mar. 1, 2010 to Official Action of Oct. 27, 2009 From the US Patent and Trademark Office Re.: U.S. Appl. No. 11/335,317.

Response Dated Nov. 1, 2010 to Official Action of Aug. 4, 2010 From the US Patent and Trademark Office Re.: U.S. Appl. No. 11/609,451.

Response Dated Mar. 4, 2010 to Proceedings Further With the European Patent Application Pursuant to Rule 70(2) EPC of Jan. 4, 2010 From the European Patent Office Re.: Application No. 05759764.3.

Response Dated Sep. 7, 2010 to Official Action of Apr. 6, 2010 From the US Patent and Trademark Office Re.: U.S. Appl. No. 11/335,317.

Response Dated Sep. 7, 2010 to Official Action of May 14, 2010 From the US Patent and Trademark Office Re.: U.S. Appl. No. 11/632,476.

Response Dated Sep. 15, 2011 to Official Action of May 18, 2011 From the US Patent and Trademark Office Re. U.S. Appl. No. 11/335,317.

Response Dated Oct. 17, 2011 to Communication Pursuant to Article 94(3) EPC of Apr. 19, 2011 From the European Patent Office Re.: Application No. 05759764.3.

Response Dated Feb. 18, 2010 to Official Action of Aug. 19, 2009 From the US Patent and Trademark Office Re.: U.S. Appl. No. 11/632,476.

Response Dated Jan. 31, 2011 to Official Action of Oct. 13, 2010 From the US Patent and Trademark Office Re.: U.S. Appl. No. 11/335,317.

Supplementary European Search Report and the European Search Opinion Dated Dec. 17, 2009 From the European Patent Office Re.: Application No. 05759764.3.

Supplementary European Search Report and the European Search Opinion Dated Apr. 28, 2010 From the European Patent Office Re.: Application No. 06701330.0.

Translation of Notice of Reason for Rejection Dated Jan. 28, 2011 From the Japanese Patent Office Re. Application No. 2007-520972.

Translation of Office Action Dated Jun. 4, 2010 From the State Intellectual Property Office of the People's Republic of China Re.: Application No. 200680022991.7.

Translation of Office Action Dated Oct. 16, 2009 From the State Intellectual Property Office of the People's Republic of China Re.: Application No. 200680022991.7.

Written Opinion Dated Nov. 5, 2008 From the International Searching Authority Re.: Application No. PCT/IL08/00802.

Baxter et al. "Jet-Induced Skin Puncture and Its Impact on Needle-Free Jet Injections: Experimental Studies and a Predictive Model", Journal of Controlled Release, 106: 361-373, 2005.

Lincoff et al. "Local Drug Delivery for the Prevention of Restenosis. Fact, Fancy, and Future", Circulation, 90(4): 2070-2084, Oct. 1994.

Scheller et al. "Paclitaxel Balloon Coating, A Novel Method for Prevention and Therapy of Restenosis", Circulation, 110: 810-814, Aug. 17, 2004.

Scheller et al. "Treatment of Coronary In-Stent Testenosis With a Paclitaxel-Coated Balloon Catheter", The New England Journal of Medicine, 355(20): 2113-2124, Nov. 16, 2006.

Schramm-Baxter et al. "Jet Injection Into Polyacrylamide Gels: Investigation of Jet Injection Mechanics", Journal of Biomechanics, 37: 1181-1188, 2004.

Schramm-Baxter et al. "Needle-Free Jet Injections: Dependance of Jet Penetration and Dispersion in the Skin on Jet Power", Journal of Controlled Release, 97: 527-535, 2004.

Restriction Official Action Dated Dec. 12, 2011 From the US Patent and Trademark Office Re. U.S. Appl. No. 12/663,859.

International Search Report Dated May 2, 2007 From the International Searching Authority Re.: Application No. PCT/IL06/00087.

International Search Report Dated Apr. 9, 2008 From the International Searching Authority Re.: Application No. PCT/IL2007/001526.

International Search Report Dated May 10, 2004 From the International Searching Authority Re.: Application No. PCT/IL03/00773.

International Search Report Dated Jul. 12, 2006 From the International Searching Authority Re.: Application No. PCT/IL05/00749.

Notice of Panel Decision From Pre-Appeal Brief Review Dated Jul. 19, 2012 From the US Patent and Trademark Office Re.: U.S. Appl. No. 11/335,317.

Written Opinion Dated May 2, 2007 From the International Searching Authority Re.: Application No. PCT/IL06/00087.

Written Opinion Dated Apr. 9, 2008 From the International Searching Authority Re.: Application No. PCT/IL2007/001526.

Written Opinion Dated Jul. 12, 2006 From the International Searching Authority Re.: Application No. PCT/IL05/00749.

Walker et al. "A Simplified Technique for the Per-Catheter Delivery of Isobutyl 2-Cyanoacrylate in the Embolisation of Bleeding Vessels", Journal of International Radiology, 2: 59-63, 1987.

Examiner's Answer Dated Dec. 6, 2012 Before the Board of Patent Appeals and Interferences From the US Patent and Trademark Office Re. U.S. Appl. No. 11/335,317.

* cited by examiner

MATERIAL DELIVERY SYSTEM

RELATED APPLICATIONS

This application is a divisional of U.S. patent application Ser. No. 11/335,317 filed Jan. 19, 2006, which is a continuation-in-part (CIP) of PCT Patent Application No. PCT/IL2005/000749 having International Filing Date of Jul. 14, 2005.

This application is also a divisional of U.S. patent application Ser. No. 11/632,476 filed Sep. 4, 2007, which is a National Phase of PCT Patent Application No. PCT/IL2005/000749 having International Filing Date of Jul. 14, 2005.

PCT Patent Application No. PCT/IL2005/000749 claims the benefit of priority under 119(e) of U.S. Provisional Patent Application No. 60/587,335 filed Jul. 14, 2004, U.S. Provisional Patent Application No. 60/599,884 filed Aug. 10, 2004, U.S. Provisional Patent Application No. 60/603,262 filed Aug. 23, 2004 and U.S. Provisional Patent Application No. 60/675,477 filed Apr. 28, 2005.

The contents of the above applications are all incorporated herein by reference.

FIELD OF THE INVENTION

The present invention relates to the delivery of materials, for example, high speed intrabody needle-less injection.

BACKGROUND OF THE INVENTION

A common treatment for a blocked artery, especially a coronary artery, is PTCA, in which a balloon is inflated inside the lumen of the artery, causing the lumen to increase, while compressing the blockage and/or forcefully expanding the artery. One problem with this method is restenosis, in which the artery responds to the PTCA procedure by inflammation and inward growth. Another problem is collapse of the wall of the artery back into its lumen.

The use of a stent attempts to help with one or both problems, by providing continual support against collapse. Restenosis may still occur and common practices are coating the stent with a material that prevents vessel growth and/or using local irradiation for the same effect. Some problems have been reported with these methods, for example, thrombosis formation.

Injection of drugs from outside the body using needle-less methods is known in the art.

US application publication 2003/0083612, the disclosure of which is incorporated herein by reference describes a needle-less device for injecting drugs from outside the body.

Injection of materials inside the body is also generally known.

T. Hirano, A. Nakagawa, H. Ohyama, H. Jokura, K. Takayama and R. Shirane "Pulsed liquid jet dissector using holmium: YAG laser—a novel neurosurgical device for brain incision without impairing" Acta Neuroehir (2003) 145: 401-406, the disclosure of which is incorporated herein by reference, describes the use of a Ho:YAG laser to evaporate water in a tube and thereby creates a forward (tube axis) plume of material.

Takayuki Hirano, MD, Makoto Komatsu, Toshiro Seaeki, Hiroshi Uenohara, Akira Takahashi, Kazuyoshi Takayama and Takashi Yoshimoto "Enhancement of Fibrinolytics With a Laser-Induced Liquid Jet" Lasers in Surgery and Medicine 29:360-368 (2001), the disclosure of which is incorporated herein by reference describes the forward injection of a thrombosis dissolving material.

U.S. Pat. No. 5,614,502 Mar. 25, 1997 "High pressure impulse transient drug delivery for the treatment of proliferative diseases" and U.S. Pat. No. 6,716,190 Apr. 6, 2004 "Device and method for the delivery and injection of therapeutic and diagnostic agents to a target site within a body", the disclosures of which are incorporated herein by reference, describe methods of material delivery inside the body, including transvascularly.

W. J. Walker, I. M. Faireley "A simplified technique for the per catheter delivery of Isobutyl 2—Cyanoacrylate in the Embolisation of Bleeding Vessels", Journal of Interventional Radiology 1987 2, 59-63, the disclosure of which is incorporated herein by reference, describes the injection of glue into a lumen and against walls of an artery, in order to block it.

U.S. Pat. No. 6,280,414, the disclosure of which is incorporated herein by reference describes a tube system for delivering a drug to the wall of a blood vessel.

U.S. Pat. No. 5,713,860 issued to Kaplan, the disclosure of which is incorporated herein by reference, teaches a lumen based system including a balloon to deliver medication.

U.S. Pat. No. 5,611,775, the disclosure of which is incorporated herein by reference teaches methods of delivery of therapeutic or diagnostic liquid into tissue surrounding a body lumen. The methods include providing a catheter having an expandable member with a plurality of small apertures and advancing this catheter into the body. The member is expanded to touch or approach the lumen wall. This patent teaches use of pressures in the range of 0.75 to 10 atmospheres to create a velocity of 0.5 to 15 M/s in material ejected through the apertures.

In other clinical scenarios, it is common to employ medicines or methods which are not cell type specific in order to eliminate a certain type of cell. Many chemotherapeutic agents are generally cytotoxic. Systemic administration of these compounds causes undesirable side effects such as nausea, hair loss, appetite suppression, weight loss and lethargy. In certain types of cancer, such as urinary bladder cancer, an intrabody lumen may be infused or "washed" with a chemotherapeutic agent in order to limit systemic toxic effects. In additional clinical scenarios, a mucosal layer covering cells lining a lumen reduces a potential efficacy of "washing".

SUMMARY OF THE INVENTION

An aspect of some embodiments of the present invention relates to injecting a medicament into a target tissue by retaining the medicament within an intra-body balloon until a desired pressure is achieved and then providing a plurality of apertures through which the medicament may exit. In an exemplary embodiment of the invention, the medicament exits the balloon through the apertures at a desired velocity. Optionally, the pressure is further increased after the apertures are provided. Optionally, the desired pressure is 15 atmospheres or more. Optionally, the desired velocity is 10, optionally 20, optionally 60 M/s or more. Optionally, at least a portion of the medicament is injected intracellularly.

In an exemplary embodiment of the invention, the target tissue is located in a body lumen. Optionally, the injection is transaxial or radial with respect to the balloon. Optionally, the injection is axial with respect to the balloon. Optionally the body lumen is a blood vessel (e.g. coronary artery, pulmonary vein or peripheral blood vessel), a prostate gland, a urinary bladder, a nostril, a nasal sinus, an ear canal, an airway, a portion of the digestive tract or a portion of the female reproductive tract. Optionally, the medicament is a cytotoxic agent, for example Rapamycin or Paclitaxel. Optionally, the medicament is a fibrotic agent, optionally including collagen and/or elastin.

In an exemplary embodiment of the invention, a cytotoxic agent is injected into a target tissue. Optionally the target tissue is a portion of a blood vessel wall. Optionally the blood vessel is a pulmonary vein. Optionally, the injection causes ablation of a portion of the vessel wall. Optionally, the injection prevents transmission of an electric signal. Optionally, the velocity of injected material may reach 20 m/s, 30 m/s, 50 m/s, 100 m/s, 150 or 200 m/s or smaller, intermediate or larger speeds. In an exemplary embodiment of the invention, the cytotoxic agent contains an alcohol, optionally ethanol.

In an exemplary embodiment of the invention, ablated tissue in the pulmonary vein blocks transmission of an electric signal. Optionally, blocking of the signal relieves symptoms of Atrial Fibrillation.

In an exemplary embodiment of the invention, the target tissue is a tumor located on an inner surface of a urinary bladder.

In an exemplary embodiment of the invention, the target tissue is a tumor located on an inner surface of a digestive organ such as the stomach, small intestine or large intestine.

In an exemplary embodiment of the invention, the cytotoxic agent contains a chemotherapeutic agent and injection of the agent directly into one or more tumors spares adjacent and/or remote normal tissue from a toxic effect of the chemotherapeutic agent.

In an exemplary embodiment of the invention, the balloon delivers a medicament to cells covered by mucosa. Optionally, the cells are located in a nostril or nasal sinus. Optionally, the cells are located in a genitourinary tract (e.g. vagina, cervix, uterus, bladder or urethra). In an exemplary embodiment of the invention, the medicament is delivered to nostrils and/or nasal sinuses to provide relief from rhinitis.

An aspect of some embodiments of the invention relates to use of elongate tube(s) including ports on their side in proximity to a tissue on an inner surface of a lumen and employing a pressure pulse to inject an agent into the tissue through the ports. In an exemplary embodiment of the invention; the tube(s) are characterized in that they cannot expand to fill the entire lumen. Optionally, the delivered material is cytotoxic.

An aspect of some embodiments of the invention relates to a high speed ejection of material from radial holes formed in an intra-body balloon. In an exemplary embodiment of the invention, the balloon includes means for providing a high pressure impulse inside the balloon. Optionally, the means is within the balloon or within a short distance from the balloon, for example, 15 mm.

In an exemplary embodiment of the invention, the ejected material is used to penetrate the walls of tubular organs, for example, a blood vessel or a prostate, optionally for preventing restenosis.

In an exemplary embodiment of the invention, the walls in the balloon comprise pressure sensitive holes which open only at a threshold internal pressure level, for example, a level above regular (e.g., PTCA) balloon inflation pressures. Optionally, the spatial density and/or diameter of the holes vary along the length of the balloon, for example, to enhance uniformity of material provision and/or for other reasons, such as spatially-non-uniform treatment. In an exemplary embodiment of the invention, the drop of pressure caused by the opening of the holes is not sufficient to deflate the balloon in a period of less than, for example, 1 minute, 10 seconds, 5 seconds, 1 second, 0.5 seconds or intermediate or lesser values. In some designs in accordance with the invention, the holes are too small to pass enough material under the applied pressure to significantly deflate and/or depressurize the balloon. In some designs, additional incoming pressure is applied to the balloon which can more than compensate for pressure loss through the holes. In some designs, pressure is released through the main lumen of the balloon, in addition to or instead of the holes. Optionally, an ongoing pressure and the shape of the holes are selected to achieve a desired material injection velocity envelope shape. In an exemplary embodiment of the invention, the hole sizes are selected so that leakage at one hole will not significantly affect the pressure at other holes, at least not within a short time period, such as 10 ms, 30 ms, 50 ms or intermediate or greater times. In an exemplary embodiment of the invention, the pressure loss within such time frames is less than 30%, 20% 10% or less of the balloon base (without the impulse) pressure.

In an exemplary embodiment of the invention, a same balloon is used both for PTCA and/or stenting and for material provision. Thus, for example, the balloon can be used for PTCA at regular balloon pressures and then, when the stenosis is compressed, the pressure can be increased to eject re-stenosis inhibiting material.

In an exemplary embodiment of the invention, the balloon, at or about the holes, is in full contact with the surrounding tissue. Optionally, a minimum contact pressure is ensured.

In an exemplary embodiment of the invention, the high pressure source comprises an explosion, for example, sudden evaporation of water caused by electricity and/or energy absorption. In an exemplary embodiment of the invention, a laser light source provides the energy. Optionally, the balloon includes a mirror or target for energy distribution control, so that some or all of the energy is distributed by the target, rather than by absorption in the balloon filling. In an alternative embodiment, a mechanical means provides the impulse. For example a thin metallic or plastic plate that releases kinetic energy (e.g., due to its expansion) when irradiated by the laser light, may be used. Optionally, the laser light releases stored energy, for example, changing the shape of a shape-memory element or freeing a spring from a constraint.

Optionally, multiple pressure sources (for example multiple laser fibers to provide multiple sources of heat for expansion) are provided in the balloon.

Optionally, means are provide to direct the advancing of a resulting high pressure wave and/or shock wave.

An aspect of some embodiments of the invention relates a balloon with pressure sensitive holes that open to allow material passage only above a certain threshold pressure. Optionally, the holes are arranged radially on the balloon. Optionally, alternatively or additionally, one or more axial holes are provided. Optionally, the holes include a layer of material, for example, part of a layer used on the balloon, which layer is torn when the pressure rises and/or by a shockwave. Optionally, the holes are formed using multiple balloon layers, at least one of which is aperture. Optionally, the holes are formed during manufacture by drilling in the balloon (e.g., using a water jet, a laser, a hot needle, micro mechanical drill and/or chemical means).

Optionally, one or more apertures (or exit ports) in the balloon are created by a laser source used for injecting the material. The apertures may be, for example through or partial (blind). Optionally, a multi-fiber laser source is used and the laser light is used both for creating passages through the balloon and for increasing the pressure inside the balloon. A single pulse or a series of pulses may be used for this task, optionally pulses of different energies. Optionally, the balloon wall itself serves as a target that absorbs laser energy, and parts of which heats explosively.

In an exemplary embodiment of the invention, the threshold pressure is above a regular PTCA inflation pressure, for example, above 5, 10, 15 or 20 atmospheres.

Optionally, the balloon is strengthened surrounding the holes and/or at other locations thereon, to prevent tearing. Optionally, the strengthening is by providing a braid of material surrounding the aperture.

An aspect of some embodiments of the invention relates to a strengthened apertured balloon, which includes a plurality of holes therein and which is strengthened near the holes, to prevent tearing of the balloon at the holes. Optionally, the strengthening is by elongate elements, such as fibers, having a length comparable or greater than the balloon diameter and optionally disposed axially, radially and/or otherwise along the balloon surface.

An aspect of some embodiments of the invention relates to injection of a structural material into the walls of tubular organs. Optionally, the injection is using a balloon that contacts the walls, optionally using needle-less injection. Optionally, alternatively or additionally, one or more needles is used to inject the structural material.

In an exemplary embodiment of the invention, the structural material is a hardening material. Alternatively, the injected material does not harden.

In an exemplary embodiment of the invention, the structural material is sufficient to enhance the structure of the wall and prevent collapse thereof.

In an exemplary embodiment of the invention, the structural material is used to strengthen one or more of a stented vessel, a PTCAed vessel, an aneurysm, a prostate and/or an anastomosis region.

Optionally, the injected material is adapted to dissipate with time, be bio-absorbed and/or migrate out of the walls, for example, due to dilution in inter-cellular fluids.

According to an exemplary embodiment of the invention, there is provided a method for injecting a therapeutic agent into a target tissue, the method comprising:
(a) providing an expandable member;
(b) positioning said expandable member in proximity to the target tissue;
(c) introducing the therapeutic agent into the expandable member until a desired pressure is achieved; and
(d) creating a plurality of small apertures in the expandable member.

Optionally, the expandable member includes at least one balloon.

Optionally, (d) is performed after (c).

Optionally, (c) is performed after (d).

Optionally, the desired pressure is at least 15 atmospheres.

Optionally, the desired pressure is sufficient to cause said therapeutic agent to exit through said apertures at a speed of at least 20 meters/second.

Optionally, the therapeutic agent enters the target tissue intracellularly.

Optionally, the target tissue is located in a body lumen.

Optionally, at least a portion of said apertures are aimed transaxially with respect to said expandable member.

Optionally, at least a portion of said apertures are aimed radially with respect to said expandable member.

Optionally, at least a portion of said apertures are aimed axially with respect to said expandable member.

Optionally, the body lumen is a blood vessel.

Optionally, the therapeutic agent includes a cytotoxic agent.

Optionally, the therapeutic agent includes a fibrotic agent.

Optionally, the cytotoxic agent includes an alcohol.

Optionally, the alcohol includes ethanol.

Optionally, entry of said cytotoxic agent into said target tissue blocks transmission of an electric signal through said target tissue.

Optionally, the method is applied to ameliorate Atrial Fibrillation.

Optionally, the therapeutic agent includes a chemotherapeutic agent.

Optionally, the target tissue is a tumor.

Optionally, the tumor is located on an inner surface of a urinary bladder.

According to an exemplary embodiment of the invention, there is provided a method for reducing a toxic effect of a therapeutic agent on a non-target tissue, the method comprising:
(a) providing an expandable member;
(b) positioning said expandable member in proximity to a target tissue;
(c) introducing an amount of therapeutic agent into the expandable member until a desired pressure is achieved; and
(d) creating a plurality of small apertures, in the expandable member;
wherein said amount is sufficient to exert a physiologic effect on cells of said target tissue but insufficient to exert an effect on cells lying at a distance greater than a selected distance from said target tissue.

Optionally, the expandable member includes at least one balloon.

Optionally, (d) is performed after (c).

Optionally, (c) is performed after (d).

Optionally, the therapeutic agent enters the target tissue intracellularly.

Optionally, the positioning employs an image guidance system.

Optionally, the positioning employs an intrabody camera.

Optionally, the target tissue includes a tumor.

Optionally, the target tissue includes a tumor in a urinary bladder.

Optionally, the target tissue includes a portion of a pulmonary vein conducting an electric signal which contributes to Atrial Fibrillation.

Optionally, the therapeutic agent enters said target tissue at a concentration of at least 1 nanogram per milligram of tissue.

Optionally, the therapeutic agent includes particles with a size in the range of 1 nanometer to 100 micrometers.

Optionally, the particles include at least one metal.

Optionally, the particles include at least one nucleic acid sequence.

According to an exemplary embodiment of the invention, there is provided a method for transmucosal delivery of a therapeutic agent to cells lining a body cavity, the method comprising:
(a) providing an expandable member;
(b) positioning said expandable member within the body cavity;
(c) introducing the therapeutic agent into the expandable member until a desired pressure is achieved; and
(d) creating a plurality of small apertures, in the expandable member;
wherein said pressure is sufficient to propel said therapeutic agent through a mucosal layer to cells beneath said mucosal layer.

Optionally, the expandable member includes at least one balloon.

Optionally, (d) is performed after (c).

Optionally, (c) is performed after (d).

Optionally, the body cavity includes a nostril.

Optionally, the body cavity includes a nasal sinus.

Optionally, the body cavity includes a portion of a genitourinary tract.

Optionally, the body cavity includes a portion of a digestive tract.

Optionally, the body cavity is a nostril and/or adjoining nasal sinuses and the method provides relief from rhinitis.

According to an exemplary embodiment of the invention, there is provided a method of treating a tissue, the method comprising:
(a) bringing at least one elongate tube including a plurality of ports on its side in proximity to a tissue on an inner surface of a lumen; said tube characterized in that it cannot expand to fill the entire lumen; and
(b) employing a pressure pulse to inject an agent into said tissue through the ports.

Optionally, the agent includes a cytotoxic compound.

In an exemplary embodiment of the invention, there is provided an apparatus for injecting a therapeutic agent into a target tissue. The apparatus comprising:
(a) an expandable member including an outer wall characterized by a plurality of nascent holes therein, said outer wall defining an inner cavity;
(b) a fill mechanism adapted to introduce a therapeutic agent into said inner cavity at a desired pressure; and
(c) a release mechanism adapted to transform said nascent holes into actual holes.

Optionally, the expandable member is shaped to conform to an anatomic structure.

Optionally, the shape of said expandable member positions said nascent holes towards a target.

In an exemplary embodiment of the invention, there is provided an apparatus for reducing a toxic effect of a therapeutic agent on a non-target tissue The apparatus comprising:
(a) an expandable member including an outer wall characterized by a plurality of nascent holes therein, said outer wall defining an inner cavity, said expandable member adapted for positioning in proximity to a target tissue;
(b) a fill mechanism adapted to introduce an amount of therapeutic agent into said inner cavity at a desired pressure; and
(c) a release mechanism adapted to transform said nascent holes into actual holes;
wherein said amount is sufficient to exert a physiologic effect on cells of said target tissue but insufficient to exert an effect on cells lying at a distance greater than a selected distance from said target tissue.

Optionally, the expandable member is shaped to conform to an anatomic structure.

Optionally, the shape of said expandable member positions said nascent holes towards a target.

In an exemplary embodiment of the invention, there is provided an apparatus for injecting a therapeutic agent into a target tissue. The apparatus comprising:
(a) an expandable member characterized by at least one protrusion adapted for engagement by a lumen and at least a portion not engageable by said lumen and including an outer wall, said outer wall defining an inner cavity;
(b) a fill mechanism adapted to introduce a therapeutic agent into said inner cavity at a desired pressure; and
(c) a plurality of injection ports.

Optionally, the outer wall is characterized by a plurality of nascent holes therein and the device includes a release mechanism adapted to transform said nascent holes into injection ports.

Optionally, the shape of said expandable member positions at least one injection port facing axially with respect to said device.

In an exemplary embodiment of the invention, there is provided an apparatus for injecting a therapeutic agent into a target tissue, the apparatus comprising:
(a) an expandable member including an outer wall, said outer wall defining an inner cavity;
(b) a fill mechanism adapted to introduce a therapeutic agent into said inner cavity at a desired pressure; and
(c) at least one injection port facing axially with respect to said device.

Optionally, the outer wall is characterized by a plurality of nascent holes therein and the device includes a release mechanism adapted to transform said nascent holes into injection ports.

There is thus provided in accordance with an exemplary embodiment of the invention, a balloon for injecting material into a wall of a hollow organ of a human, comprising:
an expandable balloon body having a surface and having an axis;
at least one predefined ejection port on said body adapted for ejection of fluid therefrom, in a transaxial direction; and
an impulse source configured for and adapted to eject material out of said point at a velocity and shape suitable for mechanically penetrating tissue adjacent said port.

Optionally, the balloon is adapted for a blood vessel. Alternatively or additionally, the balloon is compliant. Alternatively, the balloon is non-compliant.

In an exemplary embodiment of the invention, said body is adapted to be pressurized during said ejection.

In an exemplary embodiment of the invention, said impulse source comprises a laser source located remote from said body and a light guide adapted to guide said source into said body to generate a mechanical impulse thereat when said laser source is activated.

In an exemplary embodiment of the invention, said impulse source comprises a target to which energy is provided from outside to generate said impulse. Optionally, said target releases energy stored in the balloon in response to said energy. Optionally, said target converts said outside energy into said impulse.

In an exemplary embodiment of the invention, said impulse source comprises a source of electricity.

In an exemplary embodiment of the invention, said impulse source comprises a mechanical pressure generator adapted to be located outside a human body containing the wall and a fluid column connecting said generator with said balloon body.

In an exemplary embodiment of the invention, said impulse source is inside said balloon body. Optionally, said impulse source comprises a mechanical impulse source.

In an exemplary embodiment of the invention, the balloon comprises at least one axial port predefined and adapted for axial ejection of fluid therefrom.

In an exemplary embodiment of the invention, said at least one port comprises a valve adapted to pass fluid under certain pressure conditions. Optionally, said body and said at least one valve are adapted so that said balloon is operable as a PTCA balloon prior to said ejection.

In an exemplary embodiment of the invention, said port comprises a weakening in said body. Optionally, said body is strengthened adjacent to said weakening.

In an exemplary embodiment of the invention, the balloon has a stent mounted thereon and adapted to deliver said stent.

In an exemplary embodiment of the invention, said at least one port comprises a plurality of ports arranged on said body.

In an exemplary embodiment of the invention, said at least one port comprises a plurality of ports arranged and configured with said impulse source to generate a non-uniform fluid ejection pattern.

In an exemplary embodiment of the invention, said at least one port comprises a plurality of ports arranged and configured with said impulse source to generate a uniform fluid ejection pattern over at least a predetermined axial length of the body.

In an exemplary embodiment of the invention, said fluid comprises a structural material adapted to affect at least one mechanical property of human tissue when ejected into the tissue.

In an exemplary embodiment of the invention, said fluid comprises an anti-proliferation bio-active component.

In an exemplary embodiment of the invention, said fluid is stored within said body.

In an exemplary embodiment of the invention, said fluid expands said body.

In an exemplary embodiment of the invention, said body comprises at least one tube on an outside of said body and wherein said at least one port is defined on said tube.

There is also provided in accordance with an exemplary embodiment of the invention, a method of treating a hollow organ, comprising:

(a) contacting an outer surface of said balloon with the inside walls of said organ; and (b) ejecting fluid away from said balloon in a radial direction and into said walls, without the use of a needle for said penetration.

There is also provided in accordance with an exemplary embodiment of the invention, a treatment balloon, comprising:

(a) an expandable body adapted for use in a lumen of a given range of diameters; and (b) a plurality of ports formed in said body and adapted to eject fluid responsive to pressure conditions in said balloon, said conditions being met only after said balloon is expanded to said ranges. Optionally, said balloon is adapted to apply PTCA prior to said ports opening. Alternatively or additionally, said plurality of ports comprises weakened portions of said body. Alternatively or additionally, said weakenings have an outside surface that is not flush with an outside surface of said balloon. Alternatively or additionally, said weakenings have an inside surface that is not flush with an inside surface of said balloon.

In an exemplary embodiment of the invention, said body comprises at least one strengthening element adjacent to said weakenings.

In an exemplary embodiment of the invention, said plurality of ports are adapted to close once a pressure on them is below a threshold value.

In an exemplary embodiment of the invention, said plurality of ports are arranged to eject material radially to an axis of said balloon.

In an exemplary embodiment of the invention, the balloon comprises an impulse source in or near said balloon and adapted to generate an impulse sufficient to open said ports.

In an exemplary embodiment of the invention, said ports are adapted to remain closed at a pressure below 15 atmospheres.

There is also provided in accordance with an exemplary embodiment of the invention, a treatment balloon, comprising:

(a) an expandable body adapted for use in a lumen of a given range of diameters;

(b) a plurality of weakenings in said body adapted to tear or open in a controlled manner under certain pressure conditions; and (c) at least one strengthening element adjacent to said weakenings.

There is also provided in accordance with an exemplary embodiment of the invention, a kit, comprising:

an ejector adapted to inject material into an organ wall, in-vivo; and an amount of structural material adapted to effect a structural change of said vessel wall without disrupting its operational integrity. Optionally, said structural material is a setting material that sets to a hardened condition. Alternatively, said structural material is a non-setting material.

In an exemplary embodiment of the invention, said structural material is mixed with a bioactive material.

In an exemplary embodiment of the invention, said ejector is a needle-less ejector.

There is also provided in accordance with an exemplary embodiment of the invention a method of treating a vessel wall, comprising:

(a) contacting a port to said wall; and (b) injecting a structural material into said wall, such that a mechanical property of said wall is mechanically affected by said structural material. Optionally, said structural material is a setting material.

BRIEF DESCRIPTION OF THE DRAWINGS

Exemplary non-limiting embodiments of the invention will be described with reference to the following description of embodiments in conjunction with the figures. Identical structures, elements or parts which appear in more than one figure are generally labeled with a same or similar number in all the figures in which they appear, in which.

DETAILED DESCRIPTION OF EXEMPLARY EMBODIMENTS

Overview

Figure 1:
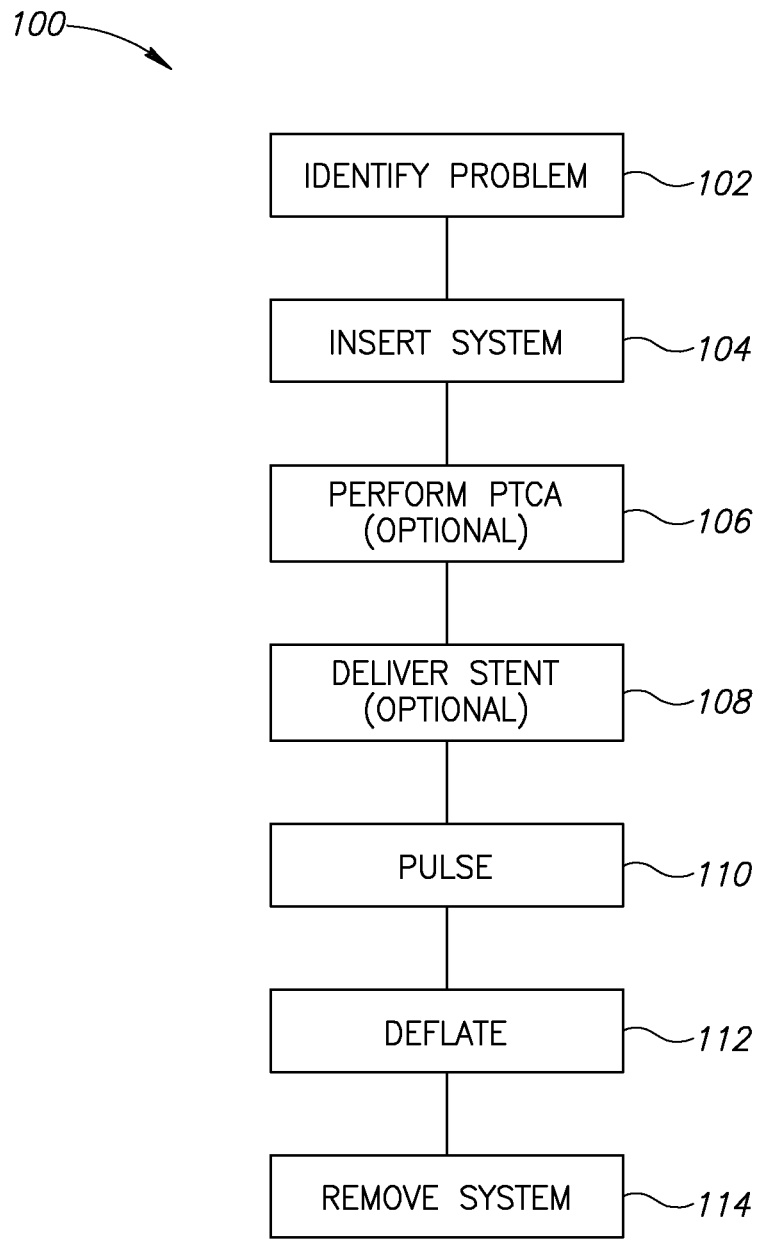
FIG. 1 is a flowchart of a method of treating blood vessels, in accordance with an exemplary embodiment of the invention.

FIG. 1 shows a flowchart of a method and FIGS. 2A-2E illustrate the acts of the method, of applying material(s) to and/or driving material(s) into the walls of a blood vessel, in accordance with an exemplary embodiment of the invention. FIGS. 2A-2E are discussed in parallel with the description of FIG. 1. Variations on the devices and/or methods are described following.

Exemplary Method

FIG. 1 is a flowchart 100 of a method of treating blood vessels, in accordance with an exemplary embodiment of the invention.

At 102, a narrowing or other problem in a wall 204 of a blood vessel 200 (FIG. 2A) is identified. Optionally, the narrowing is a plaque deposit 206, for example, a deposit with a calcified filling 202.

At 104, a catheter treatment system 210 (FIG. 2B) is inserted into the body and guided to the narrowing. Optionally, system 210 is used also to identify the problem, for example, including a contrast material port (not shown) or an imager (not shown).

A treatment balloon 212 (FIG. 2B) is shown, including a plurality of apertures (optionally initially sealed) 214, for providing treatment to walls 204.

Figure 2A:
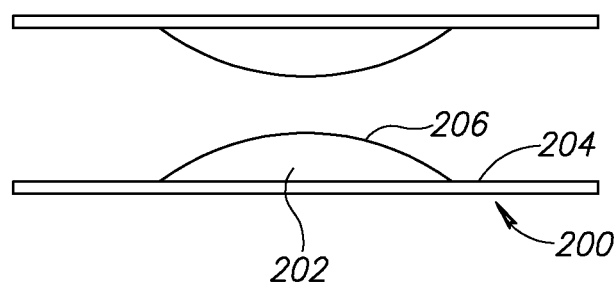
FIGS. 2A-2E are a series illustrating an exemplary process of treating a blood vessel or another tubular organ, following the flowchart of FIG. 1.
Figure 2B:
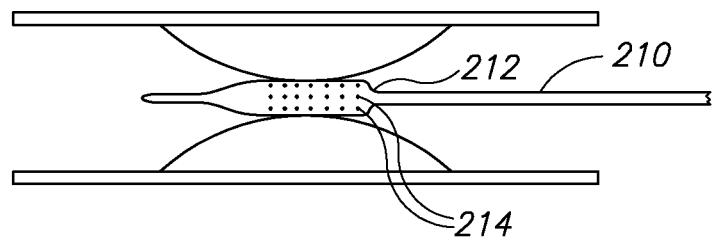
Figure 2C:
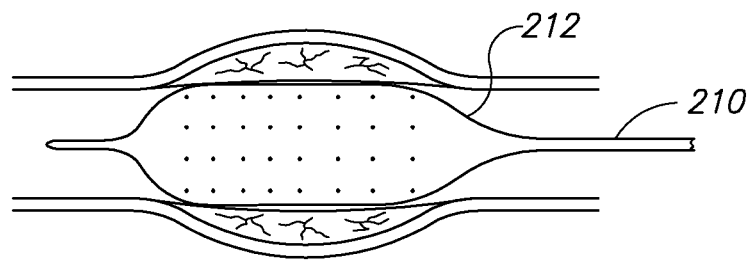

At 106, Balloon 212 is optionally inflated with pressure sufficient to perform PTCA on deposits 206 (FIG. 2C). The deposits are shown as schematically cracking. Optionally, apertures 214 leak only a small amount or are configured to remain sealed at pressures used for PTCA (e.g., 15-20 atmospheres inside the balloon).

Figure 2D:
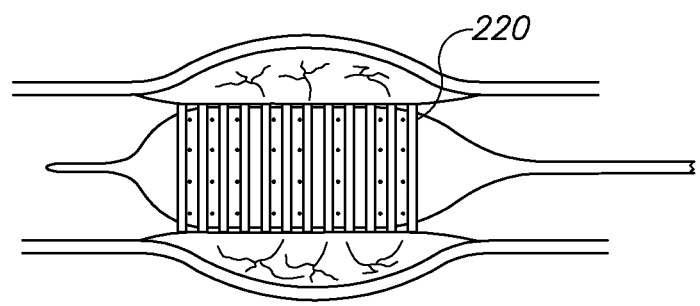
Figure 2E:
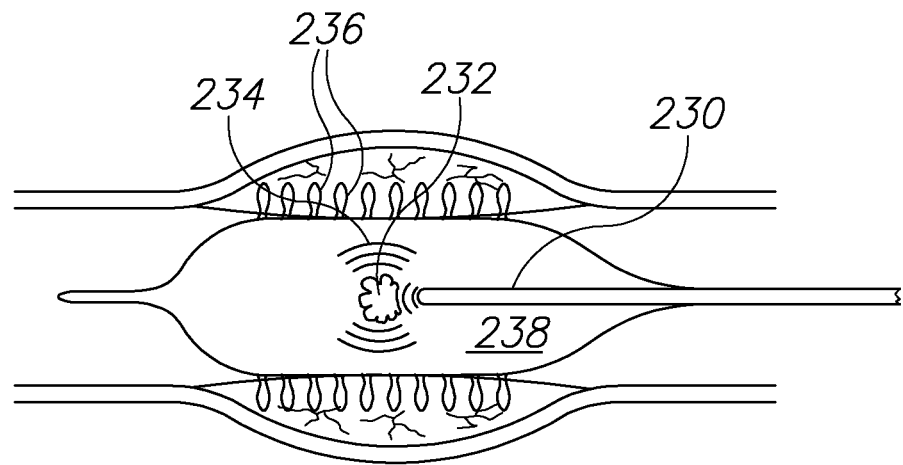

Alternatively or additionally to PTCA, balloon 212 is optionally used to deliver (108) a stent 220 (FIG. 2D).

Optionally, the stenting and/or PTCA are performed using a different balloon from balloon 212 and/or performed after provision of material to the vessel. Optionally, the material delivery method (e.g., high pressure pulse, described below) is also used to deliver the stent and/or fix it in place.

At 110, a pulse of high pressure is provided to create holes in the balloon so that one or more plumes 236 (FIG. 2E), are ejected therefrom (described below) and preferably penetrate wall 204 and/or a deposit 206 on or in the wall. In an exemplary embodiment of the invention, at least a portion of the plume is injected intracellularly. Optionally, the balloon remains inflated prior to this injection, so that contact with the wall and/or a sealing pressure, is assured. Sealing and/or contact optionally helps deliver the material at a high pressure to the wall and/or aids in its penetration into the wall.

Optionally, the delivery is at a delay after stenting and/or PTCA, for example, to allow the vessel tissue to adapt and/or to ensure the stenting and/or PTCA completed successfully. Exemplary delays are 30-90 seconds, for example, 60 seconds.

In an exemplary embodiment of the invention, an optical fiber 230 delivers a pulse of light which is absorbed in a filling 238 (e.g., saline) or a target (406 in FIG. 4), causing an explosion 232. The pulse may include a series of sub-pulses, each sub-pulse optionally characterized by a different energy. Shock and/or pressure waves 234 from explosion 232 travel to the walls of balloon 212, create holes, and cause the ejection of plumes 236. Various mechanisms which may be used are described below. In an exemplary embodiment of the invention, the plumes comprise the filling which may be, for example, saline mixed with a drug or a cement material. Optionally, the filling includes a dark (e.g. black) dye to increase energy absorbtion.

In an exemplary embodiment of the invention, the total volume of the balloon is not increased very much by the explosion, for example, the balloon diameter increasing no more than 1%, 5%, 10% or smaller, intermediate or larger values. Optionally, increase is avoided (e.g., by using a non-compliant balloon) to prevent and/or reduce pain and/or damage which may be caused by over expansion, for example, by overstenting and/or expansion of the urethra.

In alternative methods, a significant increase in balloon volume occurs, for example, 10%, 20%, 30% or a smaller, intermediate or larger value. This increase may or may not decrease after plumes 236 flow. In an exemplary embodiment of the invention, varying or cycling of the balloon diameter and/or pressure are used to assist in material penetration and/or maintenance in the tissue. In an exemplary embodiment of the invention, increased pressure after or during injection prevents leakage from the penetration points. In an exemplary embodiment of the invention, decreased pressure before injection, relaxes the vessel wall. In an exemplary embodiment of the invention, increased pressure (or waves) after penetration is used to cause sideways (e.g., circumferential) dispersion of the injected material. In an exemplary embodiment of the invention, the degree of pressure during injection controls the tissue thickness and thus the effective penetration depth.

In an exemplary embodiment of the invention, the inflation of balloon 212 guarantees that the balloon portions surrounding apertures 214 are in good contact with walls 204 of the blood vessel, possibly ensuring less leakage and/or better penetration. Optionally, a minimal contact pressure is provided, for example, 0.5, 1, 3 atmosphere or intermediate values or greater.

If a stent 220 is provided, some of apertures 214 may be created beneath a surface of the stent. However, most of the newly formed apertures will not be covered by the stent. Optionally, the apertures are arranged to fit between stent struts, however this is not essential in some embodiments, for example, due to the presence of many apertures.

If the material injection is not complete, balloon 212 may be repositioned (e.g., axially or by rotation), optionally assisted by a slight deflation to reduce contact pressure, and then additional injections carried out. Second injections may also be used if a different material is to be injected. Optionally, the same balloon is used for both injections. Alternatively, the balloon may be replaced. Optionally, two balloons are provided in tandem, for example on a same balloon catheter and/or on a same guidewire.

At 112, balloon 212 is deflated for removal 114. Optionally, some leakage occurs through the apertures during removal. Optionally, the apertures are designed to seal again when the pressure goes below a threshold, possibly a threshold lower than the injection pressure, for example, 20 atmospheres (e.g., 25% or 50% lower). Optionally, the apertures are formed of a rubber-like material that self seals when the pressure goes down. A puncture in the rubber material expands when pressure is increased. Alternatively or additionally, one or more flaps are provided on the apertures. Optionally, the flaps serve as a one way valve, allowing the flap to open outwards, but not inwards.

Figure 3:
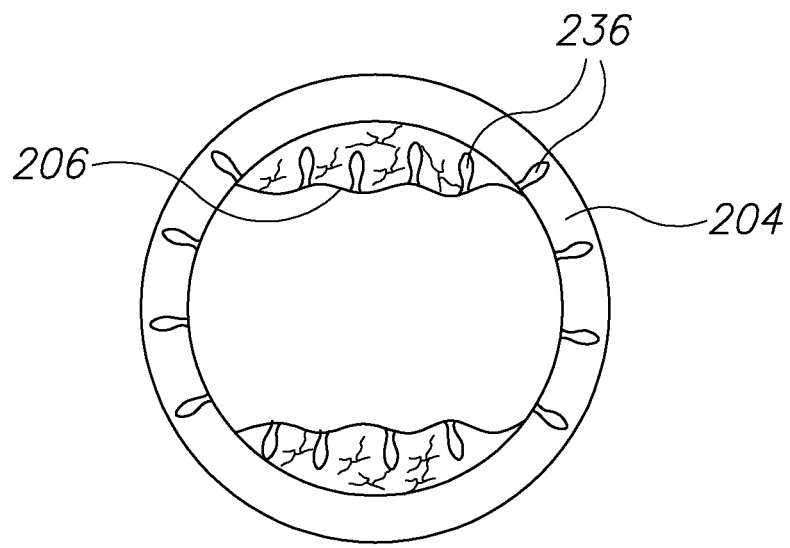
FIG. 3 is a trans-axial cross-sectional view of a treated blood vessel, in accordance with an exemplary embodiment of the invention.

FIG. 3 is a trans-axial cross-section of vessel 200 showing plumes 236 in walls 204 and deposits 206. If, for example, a structural material such as a glue is injected, it can be seen that the plumes can serve to hold the vessel open. In some embodiments of the invention, at least some of the material is provided outside of the wall. In one example, the balloon has ridges, for example in an axial or helical pattern and holes are provided at the bases of the ridges for material injection. Some or all of this injected material may remain trapped between the balloon and the vessel walls.

Exemplary System

Figure 4:
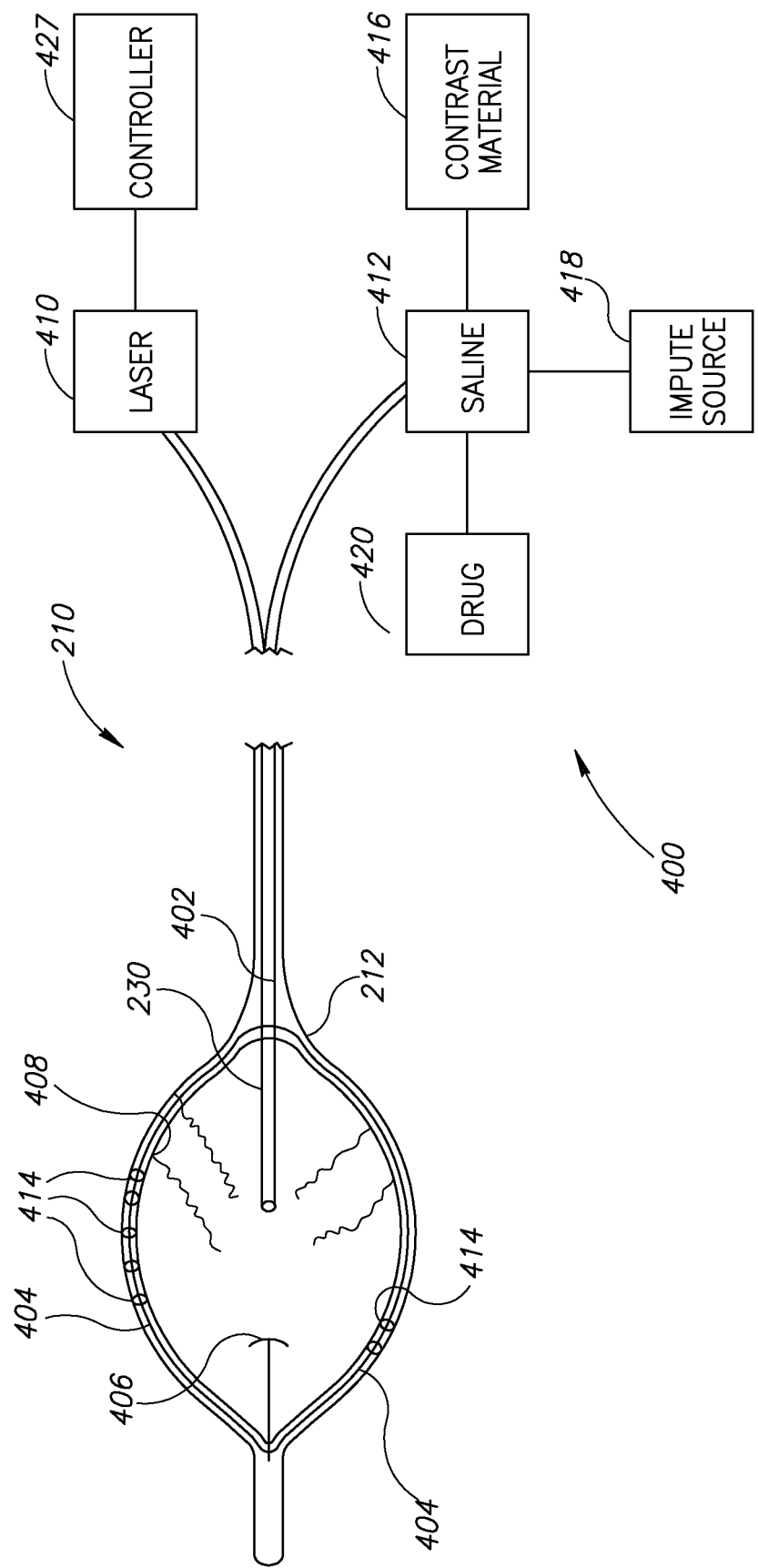
FIG. 4 is a schematic diagram of a vessel wall treatment system, in accordance with an exemplary embodiment of the invention.

FIG. 4 illustrates an exemplary system 400, such as may be used to carry out the method illustrated with the aid of FIGS. 1-3, in accordance with an exemplary embodiment of the invention.

Referring first to portions of system 400 typically outside of the body, a laser source 410 is used to provide a pulse of light for explosion 232. Optionally, a controller 427 is used to control one or more parameters of the pulse, such as total power, peak power, duration and/or repetition rate, which may serve to control the depth of penetration of plume 236 and/or an amount of material thereof, for example.

In an exemplary embodiment of the invention, temperature control of the balloon is provided. Optionally, a closed loop control, for example using a temperature sensor in the balloon coupled with fluid circulation through the balloon is used. Optionally, a heat exchanger is provided in the balloon, so the actual contents of the balloon need not be changed. Optionally, the heat exchanger is in the form of one or more coils in a lumen or a heat conducting web, such as gold. Alternatively, open loop cooling is used, for example, pre-cooling of the fluid and/or the balloon. Optionally, when a temperature of the balloon increases above a desired amount, a safety is used to warn a user and/or prevent additional energy provision. Optionally, the lumen used to provide cooling fluid is used to cool an energy providing conduit (e.g., fiber, wire).

A saline source 412 is optionally used to inflate balloon 212. Optionally, an impulse source 418 is used to generate a pressure wave in balloon 212 instead of or in addition to laser source 410.

In an exemplary embodiment of the invention, source 418 is used to generate pressure waves in the balloon, for example, to provide a massaging effect. Alternatively or additionally, vibrations are provided to the balloon, for example, to prevent adherence of the injected material to the apertures.

It should be noted that an external pressure impulse source and a laser impulse source may provide different types of effects. A laser source can provide a very sharp impulse, albeit possibly reduced volume of expulsion and/or reduced power. A pressure source, for example, a source that is outside the body, is typically capable only of less sharp impulses, however, such impulses can include considerable power and/or volume.

Optionally, both types of sources are used simultaneously, optionally in synchronization and/or with a delay between them. Each source may be used to provide one or more pulses, only some of which are synchronized.

In an exemplary embodiment of the invention, the type of source used depends on the length of the catheter. For example, in a prostate case, where the catheter is short (and volume requirements may be large) a pressure source such as a syringe, pump or gas powered system, may be used. In a coronary vessel, where the lumen delivering the pressure is long and narrow (and volume requirements are low), a laser based solution may be most appropriate.

Other impulse sources are described below.

A source of contrast material 416 may be used to provide saline 412 with contrast and/or may be used for assistance in imaging vessel 200. Optionally, other tools as known in the art are used, for example, an embolism filter.

A source of drug or other material 420 to be provided as plume 236 is optionally used as well and may feed, for example into saline source 412 or downstream therefrom. Alternatively or additionally, material 420 is used instead of and/or in addition to saline to inflate the balloon.

In an exemplary embodiment of the invention, material 420 includes a concentrated solution of a drug that optionally contains solvents and/or stabilizers. Optionally, the concentrated solution is provided as a stock solution. The stock solution is optionally provided in ampoules or syringes or vials or other sealed containers.

In an exemplary embodiment of the invention, the stock solution is diluted with saline 412 and/or contrast 416 in mixing rations of 1:50, 1:40, 1:25 or less to achieve a desired concentration. Optionally, the solution a will used to inflate balloon 212 under certain pressure.

In some embodiments, the material to be delivered, optionally including contrast material, is provided directly into balloon 212, for example by needle injection while the balloon is outside the body instead of or in addition to providing using saline (or other fluid).

In an exemplary embodiment of the invention, balloon 212 is formed of two or more layers, with one or more future aperture sites 414 formed thereon. Optionally, the future aperture sites are formed only in an inner layer and/or only in an outer layer. More details are provided below. A strengthening element 404 is optionally provided, for example, a fiber or cord. Optionally, element 404 is non-elastic and prevents over-expansion of balloon 212 above that needed for PTCA. Alternatively or additionally, element 404 is placed near future apertures 414, to prevent tears from propagating from the apertures and rupturing balloon 212.

In an exemplary embodiment of the invention, element 404 comprises a grid and the future apertures are formed in cells of the grid. Optionally, the grid is non-uniform. Optionally, a non-grid arrangement is used, for example a random felt-like arrangement or a spiral arrangement.

In an exemplary embodiment of the invention, a metal stent-like frame is used to prevent over inflation of the balloon. In one example, the stent-like cage is designed to stop expanding radially once a certain radius is reached. The balloon is inflated, and the cage prevents inflation of the balloon past that point, but still allows ejection of fluids therefrom. Optionally, the cage remains and serves as a stent. Optionally, the cage is of a spring-back type, for example formed of Nitinol.

In an exemplary embodiment of the invention, two tubes lead into balloon 212, an inflation lumen 402 and optical fiber 230. Optionally, a fluid removal lumen is provided as well (not shown) and used for replacing the contents of balloon 212 (e.g., saline by a glue material), optionally without deflating balloon 212. Optionally the optical fiber passes through the inflation lumen 402. Optionally, a separate lumen is used for the guiding wire.

Figure 6A:
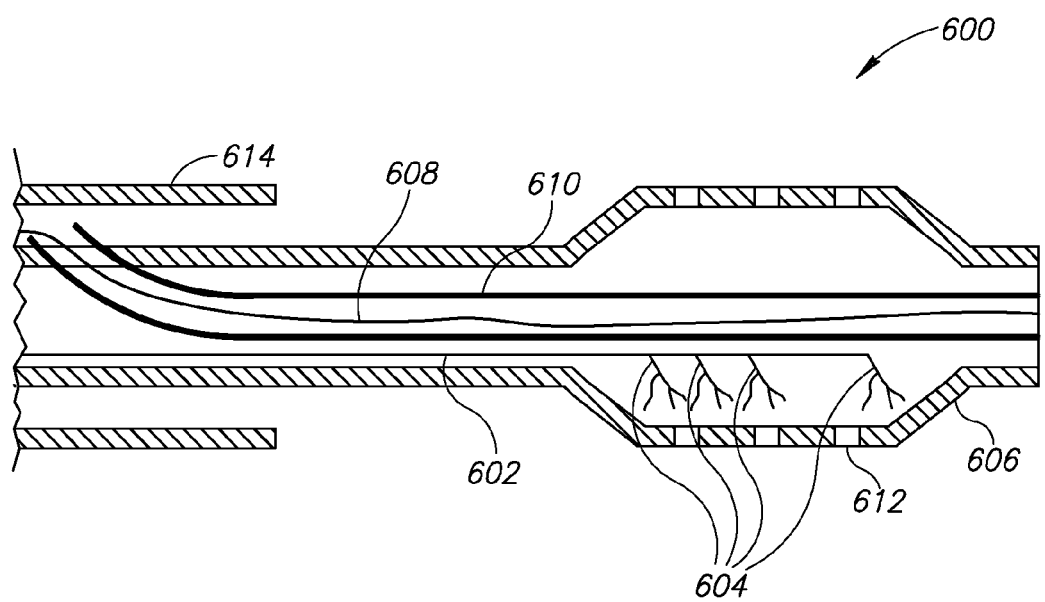
FIG. 6A-6H illustrate alternative catheter designs, some of which are suitable for prostate treatment, in accordance with exemplary embodiments of the invention.

Optionally, a plurality of fibers 230 are provided in the balloon, or a plurality of laser exiting points are provide on fiber 230, for example, to better distribute laser energy in balloon 212, for example, 2, 3, 4 or 5 exit points or more. FIG. 6A shows a system 600, in which a fiber 602 branches to multiple branches 604, each of which may serve as a local energy source. This arrangement may be used to control the distribution of shock/pressure waves in the balloon. In an exemplary embodiment of the invention, fiber 602 has a diameter of 200-220 microns and fibers 604 have a diameter of 100-120 microns each. Optionally, the diameter of fiber 602 is set by a need to transmit a sufficient amount of power. Alternatively or additionally, the diameter is determined by a need to allow bending of the fiber in blood vessels leading to the therapy area. Also visible in FIG. 6A are other parts which may be provided in a treatment system, namely a guide-wire 608 which optionally travels in its own channel 610, a balloon 606 optionally including pressure-responsive apertures 612 and a guide sheath 614.

In an exemplary embodiment of the invention, an interior framework, for example, of fibers, or a rigid attachment to the base of the balloon are provided to prevent the fiber from pointing in random directions. Optionally, the fiber is made stiff so that it stays axial. Alternatively or additionally, the fiber is attached to an inner lumen used for the guide wire and which remains generally axial. Optionally, the fiber is aimed away from any surfaces of the balloon to prevent inadvertent penetration. Optionally, nearby areas are covered with a reflective coating.

Referring back to FIG. 4, optionally, a target or mirror 406 is provided for fiber 230, to distribute and/or otherwise control the location and/or spatial extent of explosion 232. A target is optionally used to absorb the energy at the target location and a minor is optionally used to assist in redistributing the energy in the fluid filling the balloon. In an exemplary embodiment of the invention, the target is formed of carbon or aluminum oxide. Optionally, the target heats and boils fluid near it. Alternatively or additionally, the target itself explodes or evaporates at least in part. Optionally, the wavelength used by laser 410 is absorbed by the fluid used and/or by one or more impurities (e.g., dye or suspended particles) mixed therein. Optionally, the impurity is selected to selectively absorb the laser energy. Optionally, the concentration is selected so that the depth of penetration of the laser energy is a known amount and has a known effect (e.g., impulse sharpness and spatial distribution of foci). Optionally, the impurity used is the one used in eye photo-treatment, for example Indocyanine green and/or India ink. In an exemplary embodiment of the invention India ink (e.g. Spot Indian ink from GL supply company) is employed at a concentration of 2%, optionally 5%, optionally 10% or greater or lesser or intermediate concentration in order to increase energy absorption. Optionally, this increased energy absorbtion causes a more rapid pressure increase inside the balloon.

Target 406 is optionally a metal element. Alternatively or additionally, target 406 is a decomposing element, such as silver azide.

In an exemplary embodiment of the invention, the target is made of a material that absorbs the laser energy and forms a known volume of gas when hit by the laser light. Optionally, the target itself explodes. Optionally, the target comprises multiple target layers and/or a significant thickness, so that additional laser pulses will also cause evaporation of parts of the target.

Optionally, the target comprises a capsule whose shell is transparent to the wavelength used and whose contents are not.

Optionally, the target is formed on the fiber tip that delivers the laser energy, for example, as a layer of dye or metal coating.

In an exemplary embodiment of the invention, the laser source is a Nd: YAG laser and a dopant capable of absorbing at the wavelength of 1.064 microns is used. Example dopants are carbon and metal particles. Other materials that absorb between 0.800 and 1.100 microns may be used, for various laser wavelengths, for example diode lasers. Optionally, India ink may be used as described above.

In an exemplary embodiment of the invention, the laser source provides wavelengths that are absorbed in water, for example Holmium pulsed laser 2.1 microns, from an Erbium pulsed laser at 2.9 microns, or other wavelengths above 1.9 microns (for example the 1940 nm). The absorption spectrum of water is well known and wavelengths for which the absorption coefficient is high (and transmission means available) may be used. Optionally, the shock/pressure waves may be shaped by selecting a lower or higher absorption coefficient and/or different shapes for the beam. Optionally, a protective barrier is provided to prevent material affected by the laser from being injected outside of the balloon. In an exemplary embodiment of the invention, a balloon or membrane is provided around the fiber tip. Optionally, a membrane is provided inside the balloon. Optionally, while there is a fluid path between the fiber tip and the apertures, this path is indirect and significantly reduces the ejection of heat-affected material. Filling the balloon is not necessarily hampered. Optionally, the fiber tip is distanced from the apertures, for example, being outside the balloon. Optionally, a pre-defined capsule for absorbing energy and remaining sealed, is provided.

Optionally, one or more internal baffles 408 are used to guide the effects of explosion 232, for example, setting paths lengths for the shock/pressure waves, aiming the shock/pressure waves, to impinge on the balloon wall at desired angles and/or for absorbing energy and/or slowing down an impulse attack rate, in some directions. Optionally, the guiding comprises distributing the waves more evenly spatially and/or temporally.

While explosion 232 has been shown inside balloon 212, it may be provided outside the balloon, for example, within 30, 20, 15, 10, 5 or fewer mm from the inflatable part of balloon 212, for example, distally or proximally. Optionally, the area of the explosion is surrounded by a strengthening layer, for example, a layer of plastic or metal, optionally rigid, which may serve to prevent rupturing of catheter 210 and/or assist in guiding explosion waves 234 towards the balloon.

In an exemplary embodiment of the invention, the balloon is formed of standard materials, such as Nylon 12 or PET. In an exemplary embodiment of the invention, the balloon is sized for its application, for example, 1, 2, 2.5, 3 or 4 mm for relatively small vessels such as the coronaries or brain vessels. Larger diameters may be used, for example, in veins and in the prostate (e.g., 7-10 mm). A balloon may also be sized for treating the aorta or the abdominal aorta, for example, to treat calcifications or an aortic stenosis.

Exemplary Provided Materials

Structural Materials

In an exemplary embodiment of the invention, the injected material is a structural material which changes the structural (e.g., mechanical) properties of the tissue it is injected into. An example of a structural material is a glue or cement which hardens, for example, Bioglue Surgical Adhesive, Dermabond cyanoacrylate or collagen (in certain forms). Optionally, a non-hardening material is used, for example, silicon gel, carbon nano tubes, collagen (in certain forms), carbon fibers, plastic fibers and/or glass fibers. It is noted that the purposes of stiffening and/or strengthening blood vessels to prevent collapse and/or dissection thereof may be served even if the entire wall 204 is not made rigid. Various amounts of material may be injected based on the material used and/or effect desired. For example the injected material may comprise 5%, 10%, 20%, 30%, 50% or a smaller, intermediate or larger percentage of the volume of the tissue. Optionally, the injection is not spatially dense, for example, there being non-injected areas, for example of dimensions of 0.3 mm, 0.5 mm, 1 mm, 2 mm in minimum or maximum extent. Optionally, the injection fills only part of a thickness of the tissue, for example, not reaching substantially to within 10% of the edge of the tissue. Optionally, the injected material collects in certain spatial forms, for example elongate needle, where the length (radial) to width ratio is less than 1:1 or 1:2. Another exemplary arrangement is a flat arrangement, where a plume has a height to width ratio of 2:1, 3:1 or more. Generally, a smaller amount of injected material is desired provided the desired mechanical and/or biological changes are achieved.

In an exemplary embodiment of the invention, after injection, wall 204 changes elasticity, for example, increasing if an elastic material was injected or decreasing if a malleable material was injected.

Optionally, the structural material is mixed in with a bioactive or other material, for example of a type described below.

In an exemplary embodiment of the invention, the structural material is of a type not normally present in the tissue into which it is injected, at least not in significant amounts.

Optionally, the structural material is provided instead of or in addition to a stent. Optionally, a less stiff stent is used due to the provision of structural material. Optionally, the stent, accompanied by the glue injection, is at least 50%, 70%, 80% or more flexible that a standard suitable stent and/or there is reduction in metal content of 50%, 70%, 80% or more. In an exemplary embodiment of the invention, reduction in metal thickness allows stenting in small ducts, for example, smaller than 2 mm, 1 mm, 0.7 mm, 0.5 mm or smaller intra body ducts. Optionally, the amount of material in the stent is reduced as compared to an indication assumed to be correct by a physician. Optionally, a softer material is used for the stent, for example thin (as opposed to thick) plastic. Optionally, the stent is made biodegradable/absorbable, for example, biodegradable plastic or sugar. Optionally, a biodegradable stent is made more safe by the stent adhering to structural material (e.g., glue) injected by the balloon into or near the vessel walls, so that as the stent decomposes, the vessel wall prevents larger pieces of the stent from going with the blood flow.

Optionally, the reduction in stent material amount may reduce complications.

Optionally, the structural material comprises fibers, optionally fibers that are curled shut and coated with a material, such as sugar or certain plastics, which will dissolve and release the fibers after time.

Optionally, the material is dissipated when not in solid tissue (e.g., when in a blood flow) and/or dissolves. Optionally, the material is biodegradable. Optionally, these properties are used to reduce danger if the glue penetrates tissue past the blood vessel wall.

Optionally, the material hardens in contact with tissue and/or blood.

Optionally, the injected material comprises a suspension of particles. Optionally, the suspended particles will conglomerate and have a structural effect when inside the tissue, where fluid may be squeezed out and/or migration is in narrow channels. In the blood, such particles will disperse. Optionally, the particles set after time, once they meet. Optionally, the particles are selected to be of a size comparable to endothelial pores (or larger) and/or comparable in size to inter cellular spaces.

Optionally, a two part material (for example PMMA) is used, in which a first component material is injected into the walls and then a second component material (e.g., a catalyst or hardener) is injected. It is expected that such materials will dissipate in the blood stream, preventing sufficient concentrations of the materials from meeting and/or interacting with each other. Optionally, the heat provided during such a reaction is used to further prevent restenosis.

In an exemplary embodiment of the invention, balloon 212 is moved after injection of the material, to prevent sticking of the material thereto. Optionally, the balloon is rotated during a setting time of the material. Alternatively or additionally, a clean saline (or other physiologically acceptable) solution is "sweated" out of balloon 212, at a low pressure, which sweating cleans out apertures 414 and/or removes any surface residue of the injected material. Optionally, the sweated material includes a catalyst or solvent that prevents hardening of the injected material. Optionally, the balloon is coated with a material to which the structural material does adhere, for example Teflon or a silicon oil coating. Optionally, the balloon is removed before the material completes a setting process, for example, using a material with a 30 minute setting process and removing the balloon after 5 minutes. Optionally, a timer is provided with kit for using the system, which timer indicates when it is time to remove the balloon and prevent setting.

Optionally, the balloon is kept inflated while the glue hardens or semi-hardens. Optionally a blood flow bypass pathway is provided in the balloon, for example, a conduit, as known in the art.

In an exemplary embodiment of the invention, the balloon includes a pressure sensor, used to measure the response of the wall of the vessel to applied pressure and thus assess the effect of the treatment.

Dye and/or Radio-Opaque

Alternatively or additionally to a structural material, a dye/marker is injected. Optionally, the dye is used to identify regions in a later treatment (e.g., an extent of cancer, for surgery). Alternatively or additionally, the dye/marker is a radio-opaque material, which serves as an indication of stent position or treatment location. Optionally, the injection is patterned, for example so that a particular treatment and/or parameters thereof can be read from an image of the treated vessel.

Optionally, a dye component is used to estimate the amount of material injected into the vessel walls and/or lumen.

Softening Materials

In an exemplary embodiment of the invention, a material that softens plaque and/or other tissue is injected. Optionally, this injection is made prior to a PTCA procedure, so that the PTCA procedure will not only flatten the plaque but also drain it. Optionally, a structural material is injected after PTCA and/or softening. Optionally, a drainage hole is formed in the plaque for draining the softened plaque, for example, using an advancable sharp tip in the catheter, for example, provided along the guidewire or extending out of the balloon. Optionally, a suction lumen is provided to suck out the plaque. Optionally, the sharp tip is provided along the suction lumen.

Bioactive Materials

In an exemplary embodiment of the invention, the injected material is a bioactive material, for example, a material which prevents inflammation and/or tissue proliferation, such as Rapamycin taxol, immune-sensitizing or desensitizing drugs and/or gene therapy substances. Optionally, the material is encapsulated, for example, in nanoparticles, so that a slow release over a period of time such as 1-3 months is provided. Other exemplary periods are less than a week, between a week and a month and between three and six months or more.

Optionally, the bioactive materials supplement the structural material, for example, the structural material having a short term effect before the structural material dissipates, while the bioactive materials have a longer effect, such as causing fibrosis. An example of such a pair is PLA and Rapamycin. Optionally, the short term effect is immediate or starts within a few minutes or hours, for example up to a day or two. A long term effect, for example, lasts several months or years and may start, for example, after a day or a week.

In an exemplary embodiment of the invention, the methods and/or apparatus in accordance with some embodiments of the invention allow a reduction in volume of drug and/or other material used. In an exemplary embodiment of the invention, insertion directly into the tissue, and optionally with a small penetration hole which may self-seal, reduces leakage into the blood and possible side effects thereof. Optionally, the balloon remains inflated after ejection of the material, to prevent further leakage. In an exemplary embodiment of the invention, the surface to volume ratio of the material is better than for surface application, due to the high pressure which can, for example, ensure multiple narrow and deep insertions of the material into the vessel. In an exemplary embodiment of the invention, the use of needleless injection using short impulses may cause less pain to the patient and/or shorten treatment time.

In an exemplary embodiment of the invention, the bioactive material is DNA or other genomic material, such as RNA (of various types), viruses, and plasmids.

In an exemplary embodiment of the invention, the amount of injected material is less than 10 cc, for example, less than 1 cc, for example, 0.01-0.03 cc for a coronary blood vessel.

In an exemplary embodiment of the invention, the injected material is prepared and/or provided near or at the treatment time, for example, for pharmaceuticals with a short life time.

Cytotoxic Materials

In some exemplary embodiments of the invention, the injected material is a material. Examples of cytotoxic materials include, but are not limited to, chemotherapeutic agents, organic solvents (e.g. alcohols), fibrotic agents and metals (e.g. gold). Fibrotic agents may include, but are not limited to, formalin, papavain and curare. Fibrosis in the target tissue may block an electrical signal. Cytotoxicity may be desirable, for example in tumor treatment or other targeted tissue ablation. Targeted tissue ablation may have applications, for example, in treatment of atrial fibrillation and/or to mimic the effects of intestinal resection.

Aperture Manufacturing Methods

Various methods may be used to manufacture the apertures (214, 414). FIGS. 5A-5D illustrate various designs which assure that the future apertures remain sealed until a desired pressure is reached within the balloon. In an exemplary embodiment of the invention, a PTCA procedure is performed by inflating the balloon to a pressure below the desired pressure which creates apertures. Optionally, apertures are created when material injection is provided. Optionally, the apertures are 20 microns, 30 microns, 50 microns, 100 microns or other smaller intermediate or greater, dimension, in size. Optionally, the center-to center distance is 0.3 mm, 0.5mm 0.7 mm or a smaller, intermediate or greater distance.

In some embodiments of the invention, a balloon is formed first and then the apertures are formed. In other embodiments, a first layer is formed with apertures and then a second layer, without apertures is provided on top of it or beneath it (see FIG. 5E).

Figure 5A:
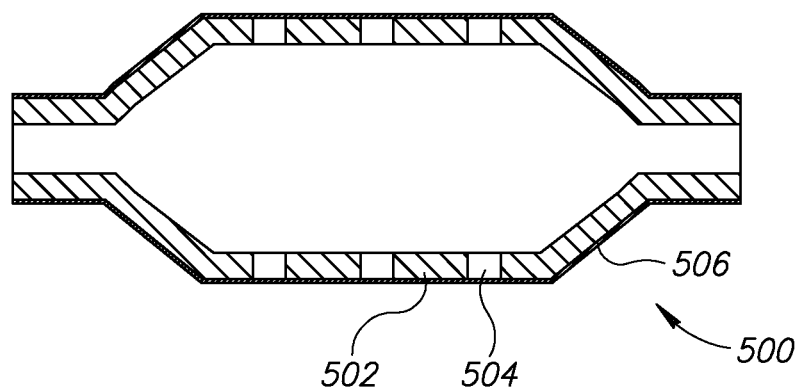
FIGS. 5A-5G illustrate pressure sensitive holes, in accordance with exemplary embodiments of the invention.

FIG. 5A shows a balloon design 500 with these later set of properties, in which an inner layer 502 has a plurality of nascent apertures 504 formed therein and an outer layer 506 is continuous. Optionally, this design prevents negative interaction (such as clotting) between apertures 502 and surrounding blood. According to this embodiment of the invention, apertures are created when layer 506 is ruptured at points corresponding to nascent apertures 504.

Figure 5B:
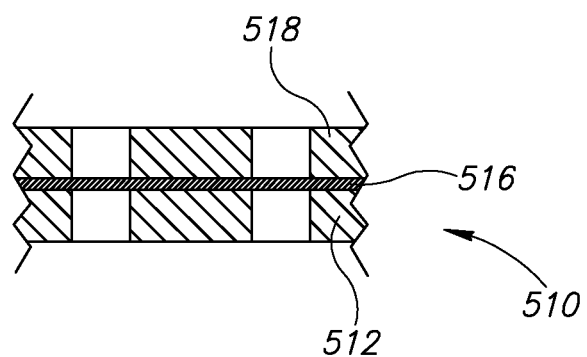

FIG. 5B shows an alternative design 510 in which a solid layer 516 is provided between nascent aperture layers 512 and 518. Optionally, the outer apertures are provided with a material that prevents clotting. According to this embodiment of the invention, apertures are created when solid layer 516 is ruptured at points corresponding to the nascent apertures in layers 512 and 518.

The strength of the solid layer and/or depth of the apertures are configured to have desired properties of tearing only above a desired threshold pressure.

Figure 5C:
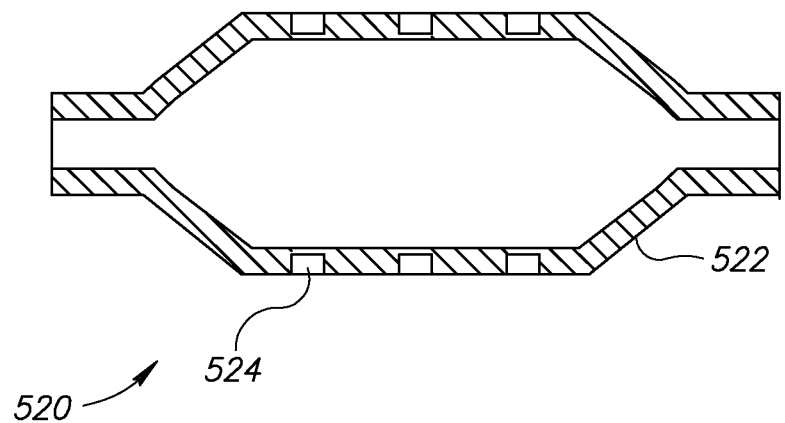

FIG. 5C shows a design 520, in which a plurality of nascent apertures 524 are formed in a single layer 522 of a balloon. Optionally, the thickness of the layer at the hole is 20-95% of the wall thickness of the balloons. Optionally, the layer at the hole is pre-weakened, for example, being punctured.

In an exemplary embodiment of the invention, an Eximer or other laser type is used to ablate material from the balloon, thereby forming the nascent apertures. Optionally, a light reflecting layer is provided between two balloon layers, to control laser penetration. Alternatively or additionally, the absorption properties of the two layers may be different. Optionally, different layers are formed of different materials.

In an exemplary embodiment of the invention, hot needles are used to form through or blind apertures in balloon 212.

In an exemplary embodiment of the invention, a water jet is used to drill the nascent apertures.

Optionally, a mask is used during nascent aperture formation to prevent damaging the balloon except at areas where a nascent aperture is desired.

In an exemplary embodiment of the invention a mold, used to manufacture the balloons, contains micro protrusions that make nascent holes, for example, when forming the balloon by blowing a plastic tube in the mold. Alternatively or additionally, the mold and/or the blown tube are covered with grains of salt or another water-soluble and/or biocompatible material, which is later washed off, leaving pores.

Figure 5D:
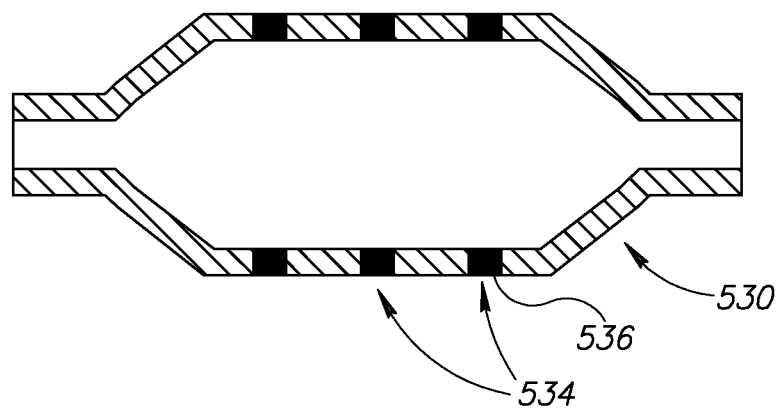

FIG. 5D shows a balloon design 530, in which a plurality of apertures 534 are filled with a temporary filling 536. When filling 536 goes away (on its own or is removed), the apertures are created. In an exemplary embodiment of the invention, filling 536 is a material the dissolves in body fluids. Optionally, the dissolution takes time, so that a PTCA procedure can be carried out before dissolution and weakening of balloon 530. Alternatively or additionally, filling 536 weakens at body temperatures. Optionally, it is not filling 536 that weakens, but an adhesive that attaches it to the rest of balloon 530 which weakens. Optionally, a non-weakening section is provided so the filling will remain attached to the balloon.

In an exemplary embodiment of the invention, filling 536 is dissolved using a solution inside balloon 530, for example, a gelatin filling or a polyspridine filling. Optionally, clot dissolving material is used to dissolve a filling made of clot-like device. Any leaking material may be useful to prevent clotting caused by the procedure (if any). Optionally, filling 536 is weakened by the inflation of balloon 530 to a maximum diameter.

In an exemplary embodiment of the invention, filling 536 does not fail due to time and/or material issues, but is weaker than the rest of balloon 530, so that while a smooth balloon surface may be presented, once a threshold pressure and/or pressure change rate is achieved, filling 536 fails and allows ejection of material.

The apertures may have various shapes. For example, the radial profile can be straight as shown. Optionally, the radial profile is cone like, which may assist in aiming the ejected material. Optionally, an hourglass or an inverted cone profile are provided.

The surface form of the aperture is optionally circular or square. Optionally, an aspect ratio other than 1:1 is provided, for example, for elongated apertures that eject a plume that has a significant width (and a relatively small thickness).

Figure 5E:
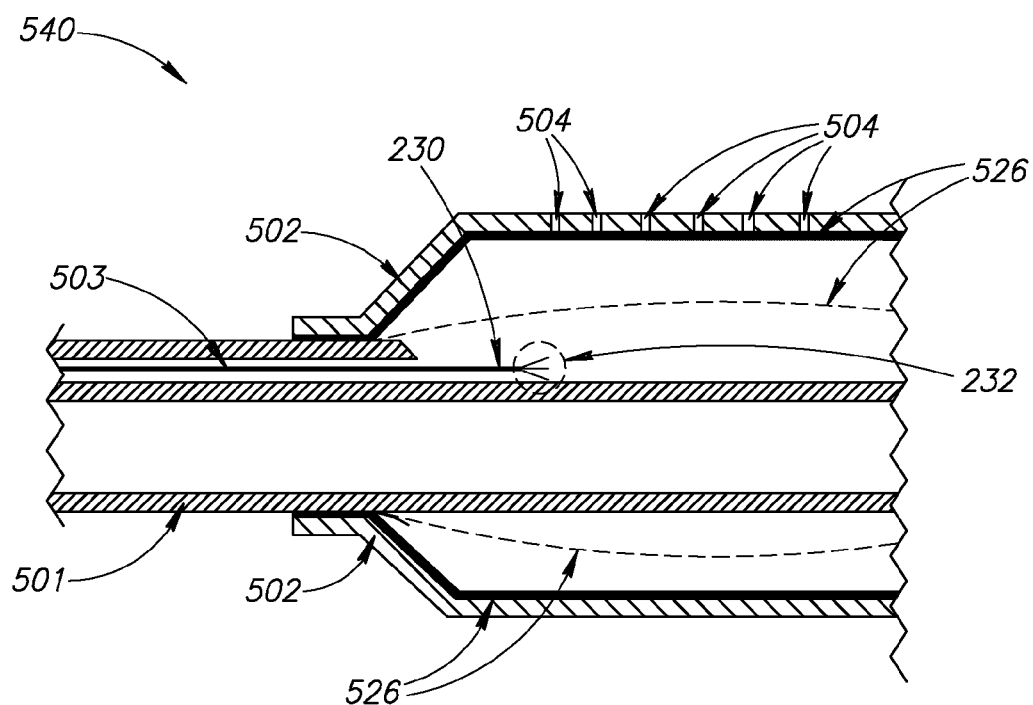

FIG. 5E shows a balloon design 540, with an additional exemplary mechanism for creation of nascent apertures 504 in main balloon wall 502. According to design 540, an inner balloon 526 expands from a deflated state (dotted lines) to an inflated state (solid lines) to seal apertures 504 by covering them from inside thereby transforming them to nascent apertures. Balloon 526 is filled with contents via lumen 503 and remains contained within balloon 502, optionally after advancing along or inside guidewire 501. Optionally, the filling of balloon 526 causes inflation of balloon 526 and/or balloon 502. In an exemplary embodiment of the invention, balloon 502 is positioned in proximity to a stenosis which is optionally crushed by an initial inflation of the balloons.

In an exemplary embodiment of the invention, an optical fiber 230 deployed through lumen 503 conducts an optical energy pulse 232 which generates shockwaves through the interior of balloons 526 and 502. Shockwaves 232, optionally from a laser energy pulse, increase the pressure within inner balloon 526 suddenly to a desired level. At most points, inner balloon 526 is supported by outer balloon 502. However, at points where inner balloon 526 is in contact with a nascent aperture 504, the sudden increase in pressure causes rupture of inner balloon 526 creating an actual aperture from the nascent aperture. Rupture of inner balloon 526 causes it to shrink to its original un-inflated diameter. This shrinking optionally occurs in about 0.03 seconds or less. In an exemplary embodiment of the invention, rupture of inner balloon 526 causes ejection of the contents outwards through apertures 504 of balloon 502 as described hereinabove. In an exemplary embodiment of the invention, inner balloon 526 is resistant to rupture at pressures of 15 atmospheres, optionally 30 atmospheres, optionally, 40 atmospheres, optionally, 50 atmospheres, optionally, 60 atmospheres, optionally 68 atmospheres optionally 75 atmospheres, optionally 100 atmospheres or intermediate or lesser or greater pressures. Optionally, outer balloon 502 does not rupture at these pressures. Optionally, the sudden release of high pressure through newly unmasked apertures 504 creates an ejection velocity of liquid of 60 m/s or more.

In an exemplary embodiment of the invention (FIG. 5E), inner balloon 526 ruptures without an applied energy pulse. One of ordinary skill in the art of engineering will be able to construct inner balloon 526 and outer balloon 502 so that inner balloon 526 is adapted to burst at a desired inflation diameter and/or volume within outer balloon 502. Construction considerations include Young's modulus, tensile strength and thickness of the materials employed to construct balloons 526 and 502. Operation of this embodiment is similar to the embodiment described above in the context of FIG. 5E except that no energy pulse is employed. According to this embodiment, inflation of balloon 526 expands it within balloon 502 transforming holes 504 to nascent holes by sealing them. At a predetermined diameter or volume, balloon 526 bursts and balloon 502 does not. This bursting of balloon 526 exposes holes 504 in balloon 502. The liquid content of balloon 526 exits through holes 504.

Figure 5F:
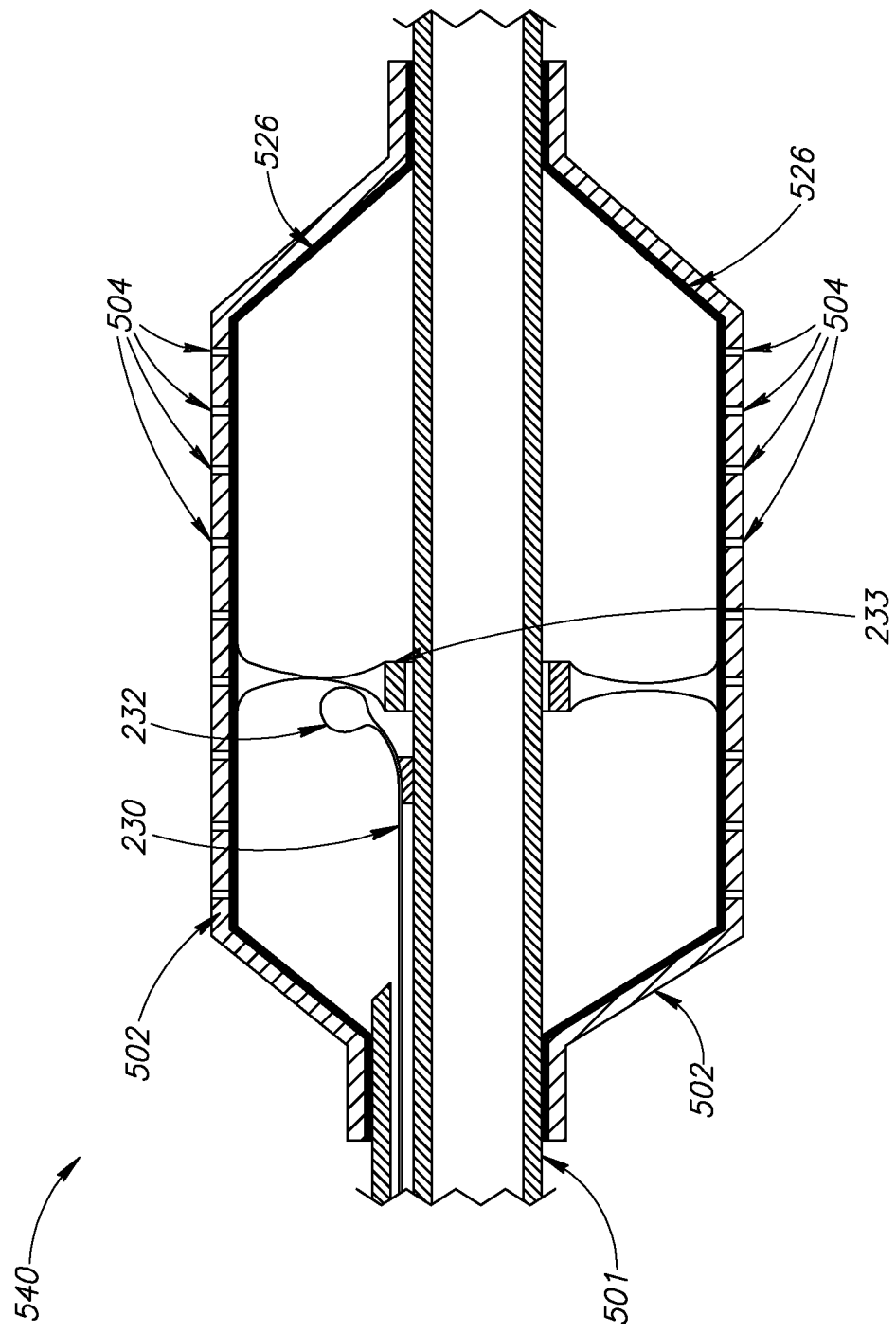

FIG. 5F shows an exemplary variation of balloon design 540 which permits rupturing inner balloon 526 separately from ejection of material via newly unmasked apertures 504. In the pictured embodiment, a portion of inner balloon 526 is stretched away from outer balloon 502 to one or more attachment points 233. Attachment points 233 are optionally radio opaque markers of the type commonly included in a conventional angioplasty balloon. Stretching brings a portion of inner balloon 526 into proximity with a distal tip of optical fiber 230. Optionally, a localized shockwave 232 is applied from distal tip of fiber 230 and ruptures inner balloon 526. Alternatively or additionally, optical fiber 230 heats radio opaque marker 233 which melts or burns inner balloon 526 and causes it to rupture. In an exemplary embodiment of the invention, the distal tip of fiber 230 is either in contact with inner balloon 526 or a short distance away (e.g. 0.2 to 1 mm). The location of distal tip of fiber 230 is near the ring 233. Ring 233 can be a radio opaque marker (e.g. gold or a gold alloy) or a restriction band or some enlargement in inner balloon 526 itself. The amount of energy delivered by the distal tip of fiber 230 in order to tear the internal balloon 526 in the stretched ring region is optionally 0.5 Joules, optionally 1 Joule, optionally 2 joules, optionally 3 joules or more.

In an exemplary embodiment of the invention, distal tip of fiber 230: delivers a second energy pulse of 3 Joules, optionally more, to eject material outwards from apertures 504. Optionally, energy pulses delivered by distal tip of fiber 230 last about 200-300 microseconds. Optionally, the two bursts of energy are applied, separated by a pause of about 0.02 to 0.1 seconds.

Alternatively or additionally, a distal tip of optical fiber 230 physically ruptures inner balloon 526 (e.g. by puncture or tearing). Rupture of inner balloon 526 causes it to shrink as explained above with respect to FIG. 5F, and permits the contents of the balloon to begin to exit through newly unmasked apertures 504 in outer balloon 502. The exit velocity of the contents at this stage is determined by the internal pressure in balloon 526 at the time of its rupture.

According to exemplary embodiments of the invention depicted in FIG. 5F, rupture of inner balloon 526, whether from an energy pulse, heating of radio opaque block 233 or from physical contact, is followed by a main energy pulse 232. Main energy pulse 232 delivered after rupture of inner balloon 526 provides a high pressure shockwave which ejects contents of balloon 502 outwards through newly unmasked apertures 504 as described hereinabove. The main energy pulse 232 is optionally provided by optical fiber 230.

In an additional exemplary embodiment of the invention (FIG. 5F) rupture of inner balloon 526 is facilitated by constructing inner balloon 526 of a light sensitive material. According to this embodiment of the invention, cumulative exposure to light weakens balloon 526. Optionally, light energy 232 is delivered via optical fiber 230 and weakens inner balloon 526. Optionally, light energy 232 is characterized by a first wavelength. In an exemplary embodiment of the invention, a main energy pulse 232 (optionally characterized by a second wavelength) causes weakened balloon 526 to rupture and permits ejection of contents through apertures 504 at high velocity as described hereinabove.

Figure 5G:
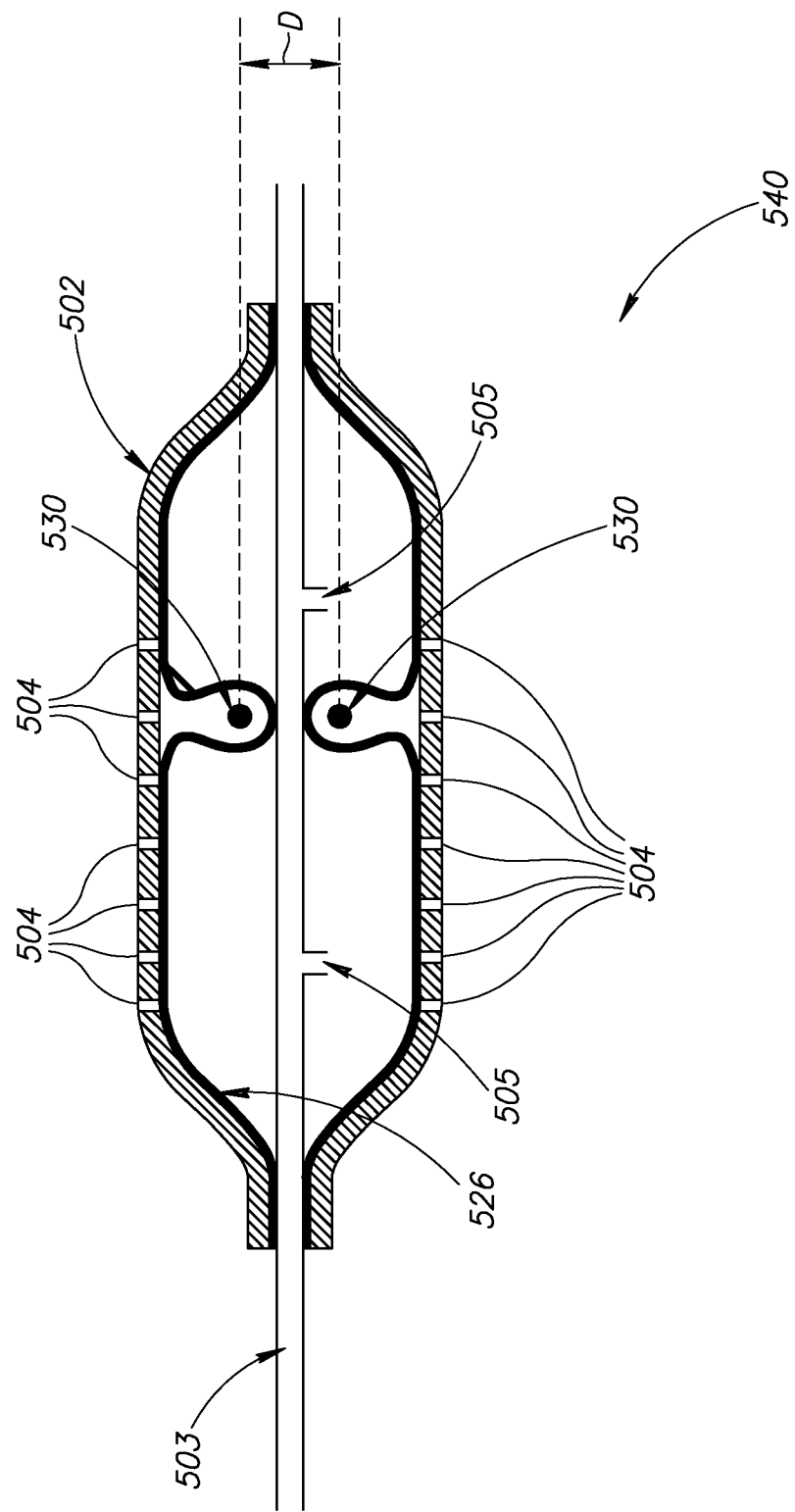

FIG. 5G shows an exemplary variation of balloon design 540 in which rupturing inner balloon 526 leads directly to ejection of material via newly unmasked apertures 504. The pictured embodiment is operable without a laser. In the pictured embodiment, a ring 530 with a diameter (D) constrains inner balloon 526. As inner balloon 526 inflates, it is stretched away from outer balloon 502. The critical inflation pressure at which inner balloon 526 bursts varies with D and/or a thickness of balloon 526 and/or a material from which balloon 526 is constructed and/or a conformation of the portion of ring 530 which contacts balloon 526. In an exemplary embodiment of the invention, an increase in D causes the critical inflation pressure at which inner balloon 526 bursts to increase. Inflation of inner balloon 526 is optionally via holes 505 in lumen 503. In an exemplary embodiment of the invention, the critical inflation pressure at which inner balloon 526 bursts is 10, optionally 12, optionally 14, optionally 16, optionally 18, optionally 20 atmospheres or lesser or greater or intermediate values. As in embodiments described hereinabove, rupture of inner balloon 526 transforms nascent apertures 504 into actual apertures. Material flows outward through these apertures and is injected into surrounding tissue.

Balloon Filling

While, in an exemplary embodiment of the invention, the balloon is filled using lumen 402, optionally, at least the injected material is not provided through the lumen, for example, to prevent clogging thereof and/or to reduce waste.

In an exemplary embodiment of the invention, injection is into the balloon via a one way valve in the balloon, for example, injection through a rubber plug at a tip thereof.

In an exemplary embodiment of the invention, material is provided as a layer on the inside of the balloon. Optionally, a two layer balloon is provided, with the material to be ejected provided between the layers and the apertures provided only in the outer layer. Optionally, the outer layer is provided as a cap which can be mounted on an existing balloon design, for example, being adhered to the base of the balloon and/or catheter.

In an exemplary embodiment of the invention, two balloons are provided in tandem on the catheter, with one balloon (for example the distal balloon), being a PTCA balloon and the second balloon (for example the proximal balloon), being a material injection balloon. Optionally, different lumens are provided for each balloon. This optionally allows for lower pressures and or a more structured balloon to be used for material insertion.

Injection Patterns

The actual pattern of the injected material may vary. In some embodiments of the invention, the system is manufactured to have a desired pattern. Alternatively or additionally, the pattern may be controlled, for example, using controller 427 or other means, for example, by varying the balloon pressure during the procedure or by varying the pulses of the laser thereby modifying the shape of the pressure/shock waves.

In an exemplary embodiment of the invention, the pattern of injection is decided based on one or more of:

(a) type and/or wall properties of blood vessel, such as thickness;

(b) resistance of vessel to inflation (e.g., feedback to saline source 412);

(c) type of plaque;

(d) X-Ray image of the area to be treated, from before or during the treatment;

(e) nearby structures which may be damaged or otherwise affected by spill of the injected material;

(f) type of mechanical modification desired for blood vessel;

(g) previously missed (un-treated) areas; and/or (h) length of stent vs. length of damaged area.

These may be used, for example, to decide on the type of structural support and/or drug treatment and/or other treatment desired for the lesion.

In an exemplary embodiment of the invention, the depth of penetration is controlled by the power and/or duration of the pressure pulse and/or its increase rate. Optionally, penetration depth is controlled, for example to ensure that all desired layers of a vessel wall and/or plaque are treated and/or to control over-penetration past the vessel wall.

Optionally, the direction of penetration is modified by changing the angle of the apertures relative to the balloon (e.g., to not be perpendicular as shown).

In an exemplary embodiment of the invention, uniformity of material injection is controlled by one or more of non-uniform distribution of apertures and/or non-uniform size of apertures, so that the total amount of plume material per unit area is the same, for example, taking into account a non-uniform pressure profile inside the balloon. Optionally, for new materials, for example, with different compressibility and/or acoustic velocity than water, the sizes of the apertures are calculated by experimenting with different apertures sizes to determine the effect of explosion on the transport through different apertures. Optionally, instructions are provided with a kit explaining what hole sizes and/or pressure profiles to use for what materials and/or lesions.

In an exemplary embodiment of the invention, the aperture sizes and/or number are such that there is no significant pressure loss from the apertures that first start ejecting material, before the other apertures tear and start ejecting material. Optionally, additional material is provided through the lumen, under pressure, to maintain the intra-balloon pressure.

In some cases, non-uniform injection is desired. Optionally, the non-uniformity complements stent design, for example, additional material being injected at the ends of a treated area and/or past a stent position and/or at points where the stent (or stent support) is weaker. In an exemplary embodiment of the invention, injection is provided between stent struts, where support is less.

In an exemplary embodiment of the invention, different materials and/or amount of materials are injected for plaque and vessel wall and/or for different plaque types. Optionally, the balloon includes a radio-opaque marker that indicates a rotation of the balloon on an x-ray image. Optionally, different balloons are used for providing lobes of material in different direction. Alternatively, the filling of the balloon may be replaced. Optionally, a same balloon is used for multiple axial and/or rotational positions relative to the treated area, with some positions the balloon being activated in a manner that increases material injection relative to other positions. Optionally, for positions with plaque in the vessel, a layer of setting material is provided at the plaque. Optionally, a material is squeezed between the balloon wall and the vessel wall (e.g., using a low pressure and optionally reduced balloon inflation pressure), so that the material can seep into cracks and/or other damage made to the vessel wall and/or plaque thereat. Optionally, this procedure is applied at known plaque positions.

In an exemplary embodiment of the invention, pre-procedure or during procedure a diagnosis of the lesion to be treated is made. Depending on the diagnosis, a desired pattern of material distribution is selected and is optionally implemented by selecting a suitably apertured balloon and/or balloon cap.

In an exemplary embodiment of the invention, the apertures are arranged in a regular grid pattern or any pattern suitable for manufacturing. Optionally, a helical pattern is used. Optionally, the holes sizes and/or distribution and/or source of pressure impulse are arranged to correspond to a known or expected plaque configuration. For example, as many vessels have a plaque lesion in a form that is thicker at the middle than near the ends, a balloon that ejects material more forcefully and/or in greater amounts near the middle may be manufactured. In special cases, other balloons, for example, which eject more at one end, are used, based on a diagnosis of the lesion to be treated.

In one embodiment, apertures are provided only on one segment (axial and/or radial) of the balloon. Optionally, this is used for partial occlusion or for selective injection such as where additional injection is needed at one side of a vessel or reduced injection is needed at a different side of a vessel.

In an exemplary embodiment of the invention, ejection (optionally sector-limited) of a structural material is used to attach a graft or a patch to a blood vessel. In an exemplary embodiment of the invention, the graft or patch to be attached is provided on the balloon and inflation of the balloon positions the patch/graft in place. Ejection of structural or bioactive material, for example, plumes that skewer the patch and the vessel or material that passes the patch and collects between the patch and the vessel, serve to fix the patch to the vessel. Optionally, one or more apertures are pre-formed in the patch or graft and aligned with the apertures of the balloon, to help material provision past the patch. Optionally, the balloon includes one or more needles thereon, on which needles the graft may be engaged and through which needs the material is optionally provided.

In another embodiment, an overtube (not shown) with an opening formed in a side thereof, is optionally provided over the balloon, so that injection can only be through apertures aligned with the opening. Optionally, the overtube is flexible and/or pleated, and is strong enough to resist the ejection pressure. Optionally, this overtube is provided once the narrowing in the vessel is expanded by the balloon.

In an exemplary embodiment of the invention, the amount of material injected is controlled by one or more of:

(a) pulse duration (e.g., pulse of laser or of pressure source);
(b) pulse shape (e.g., square, triangle or sinus);
(c) number of pulses;
(d) delay between pulses;
(e) contact pressure;
(f) energy in a pulse; and/or
(g) combinations of the above, for example, a long train of short pulses as compared to a short train of longer pulses.

In an exemplary embodiment of the invention, energy amounts and the spatial and/or temporal density of provision is selected to not damage the blood vessels. For example, it appears that in some cases, a 3.5 Joule pulse is too strong for coronary vessels and the injected material will pass through and past the wall. For example, a 0.15 Joule pulse of 300 microsecond length, applied to 100 holes of 30-50 micron diameter has been found to not perforate a coronary vessel and also not penetrate the wall with the injected material. While these numbers may depend on various factors, in an exemplary embodiment of the invention, the energy in such a pulse scheme is greater, for example, 0.5 or 1 Joule or possibly 2 Joule or 3 Joule or intermediate values. If the number of holes is changed or the pulse length varied, the energy may need to be changed in an appropriate manner. In cases where it is desirable to pass past the coronary vessel walls, a greater energy may be used, for example, 4 Joule, 5 Joule, 7 Joule, 10 Joule or more.

In an exemplary embodiment of the invention, one or both of two transport mechanisms may be optionally and/or selectively used, a pressure impulse wave mechanism, where a sharp increase in internal balloon pressure causes part of the balloon filling to leave through the apertures, and a fluid induced laser shockwave transport method, where a high speed heating of fluid at a point generate a bubble gas which causes material to be ejected with force.

In an exemplary embodiment of the invention, in a pressure type system, a stroke and pressure applied by an external piston is controlled, the stroke length controlling the amount of material ejected and the force and envelope of the stroke controlling the penetration depth. Optionally, the stroke length is manually or automatically settable, for example, by moving a stop.

In an exemplary embodiment of the invention, in a shock wave (laser ablation of water) system, the volume and depth penetration are controlled by modifying one or more of energy per pulse, pulse duration, and number of pulses.

In some embodiments of the invention, both patterns are used, for example, utilizing a larger volume effect of the pressure mechanism and a lower volume but higher speed injection of the shock effect.

Alternative Impulse Generation Methods

In an exemplary embodiment of the invention, a sudden increase in pressure and/or generation of shock waves inside the balloon is generated by a different mechanism than described above. Such pressure/shock waves may also be used for other purposes, such as surface sweating of a material.

In an exemplary embodiment of the invention, instead of a laser source, an electrical spark method is used which generates a spark between two conductors under high voltage, causing an explosion and associated shock/pressure waves. While the energy may be provided by wire along the catheter, optionally it is provided using eddy currents induced by an outside-the-body magnetic field.

In an exemplary embodiment of the invention, a capsule with a compressed spring (or other mechanical element) is used as the impulse source. In an exemplary embodiment of the invention, when the capsule is heated by laser and/or electricity, the potential energy stored in the spring changes to kinetic energy which results in fast tearing or expanding of the capsule and associated waves. Optionally, the energy is stored in the spring ahead of time, for example, at manufacture. Optionally, the capsule is in two parts and the heating only allows them relative motion, but no fluid enters the capsule.

Optionally, such a capsule includes an explosive or gas forming element, such as a lump of silver azide, that when triggered, generates gas that expands the capsule and increases intra-balloon pressure.

Figure 6B:
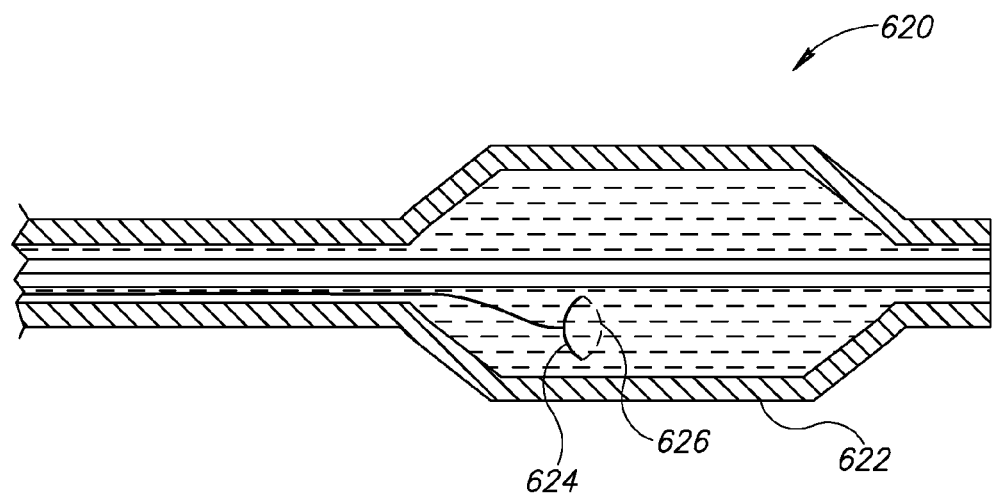

FIG. 6B shows a catheter head 620, in which a balloon 622 includes a target 624, for example, a leaf spring 624 bent to a curved shape by a strong cord (not shown in the picture, made for example of an electro-resistive material, a heat sensitive material and/or a laser light absorbing material). When heating the cord it tears, and the leaf spring jumps to a shape indicated by a reference 626, thus causes shock/pressure waves.

In an alternative exemplary embodiment of the invention, target 624 is a circular disc (or square) with a diameter of 400 microns, a thickness of 590 microns and a curve radius of 200 microns. Application of energy to the disc will cause distortion, culminating in a sudden catastrophic shape change in the disc, which change will release some of the energy provided by the laser (or other source) and cause the shock/pressure effects. Optionally, the energy is supplied at a rate higher than loss via mechanisms such as heat.

In an exemplary embodiment of the invention, the balloon and/or catheter are used as an elastic energy storage element. In an exemplary embodiment of the invention, pressure to the catheter is increased until the apertures tear and fluid from the balloon rushes out. Optionally, the parts of the catheter near the balloon and/or the balloon and/or a gas filled bladder in the balloon serve as storage areas that are near the fluid injection, so that there is a reduced loss of pressure In an exemplary embodiment of the invention a small balloon or bag encapsulate the tip of the fiber (in a laser embodiment) and heating of a material in this small balloon will generate the desired impulse.

It is noted that in several of the mechanisms described above, while there is a change in pressure in the balloon that causes material injection, the actual change in volume of material inside the balloon is minimal or zero, so that the amount of material actually injected may be small. Repeated pulses may increase the total output volume. Between pulses, topping off of the fluid pressure may be used to maintain balloon inflation.

Figure 6C:
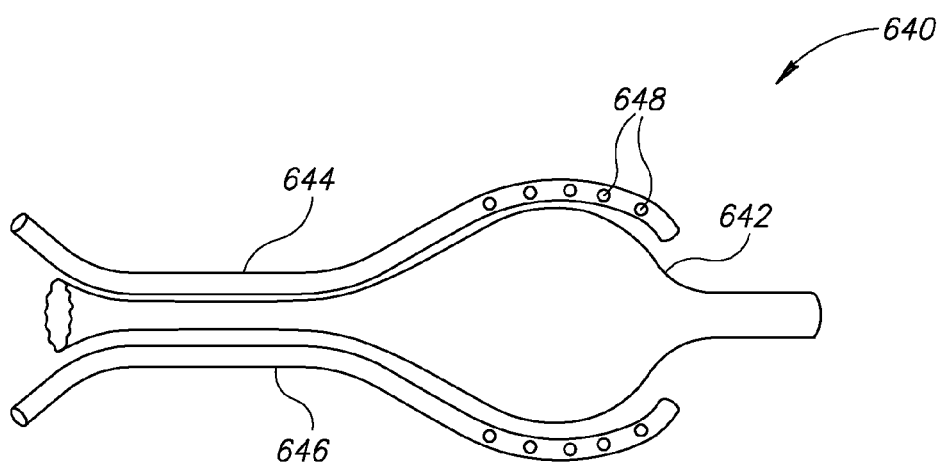

FIG. 6C shows a system design 640, in which a balloon 642 may itself have no apertures, but one or more tubes 644 and 646 are provided outside of balloon 642 and include apertures 648 for material injection, therein. Tubes 644 and 646 may be attached to each other and/or be arranged differently than shown, for example, as a spiral around balloon 642. Optionally, balloon 642 is used to ensure contact between apertures 648 and the surrounding blood vessel. Optionally, a pressure pulse is provided via tubes 644 and 648, to inject material. Optionally, an optical fiber is provided in each arm, to generate a local impulse for the arm. Optionally, tubes 644 and 648 are compressible and the pressure pulse is provided by balloon 642, for example using methods described above, whereby the pressure wave travels through the wall of balloon 642 and into tubes 644 and 648. Optionally, balloon 642 is used for rhythmically squeezing the tubes and thus pumping material out of apertures 648. A one way valve (not shown) is optionally provided in side tubes 644 and 646 to prevent backflow in the tubes.

Optionally, such external tubes are used for treating a prostate, where, in general, a larger diameter catheter may be used.

Figure 6D:
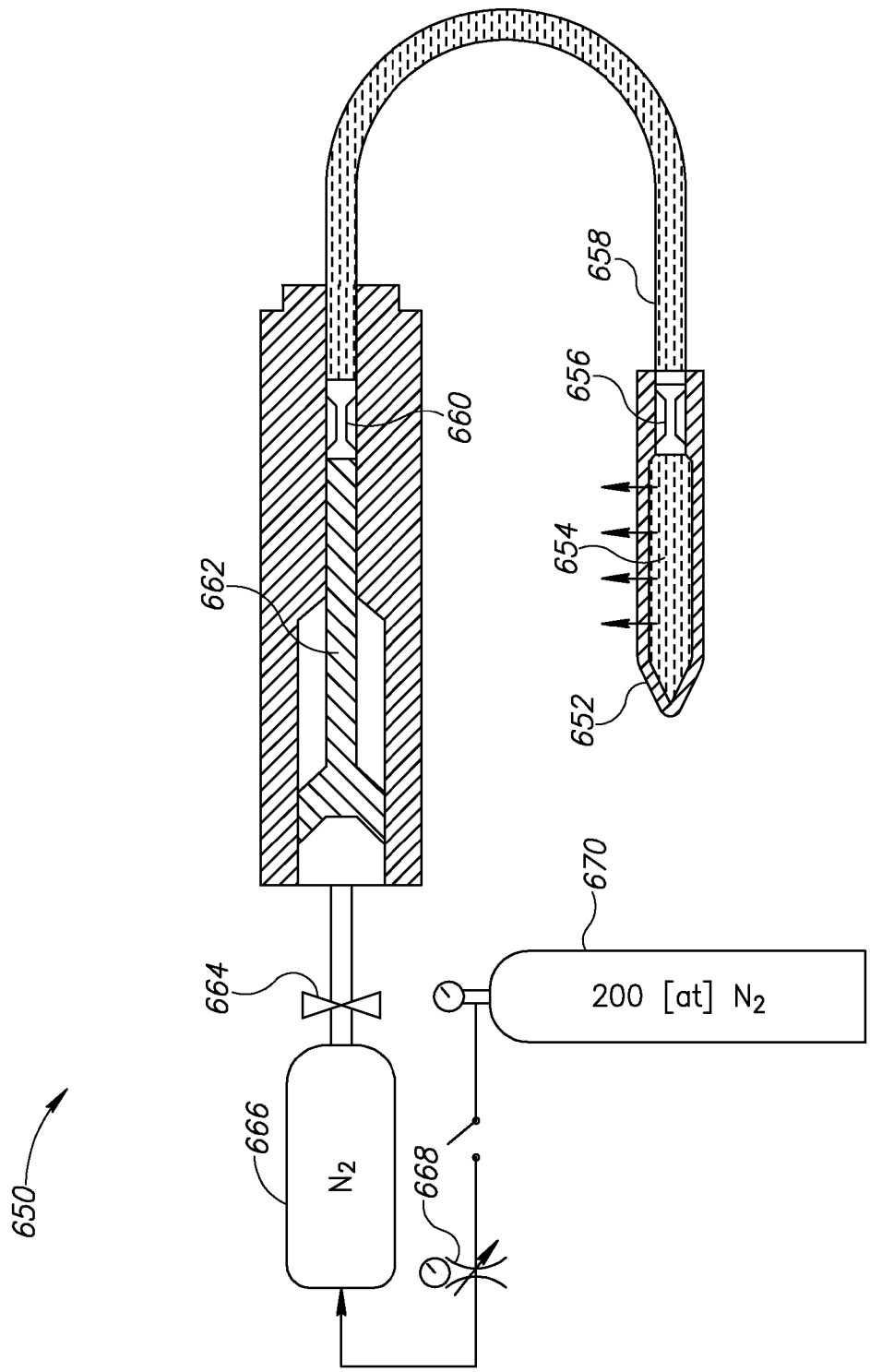

FIG. 6D is a schematic showing of a gas-powered two stage system 650 for creating a pressure impulse in a balloon 652. A gas pressure source, for example a compressed gas cylinder 670 with an optional pressure regulator 668 that is used to charge a cartridge 666, is selectively released by a valve 664. Upon release a first piston 662 is advanced, which moves a plunger 660. Plunger 660 advances a hydraulic fluid 658, optionally with a low resistance, through some or the entire catheter to balloon 652. A filling 654 of balloon 652 (which may be high viscosity) is optionally separated from the hydraulic fluid by a second plunger 656. Optionally, slow advancing of fluid 658 inflates the balloon and fast advancing causes an impulse that ejects material. The hydraulic fluid may be a closed system filled during manufacture.

Figure 6E:
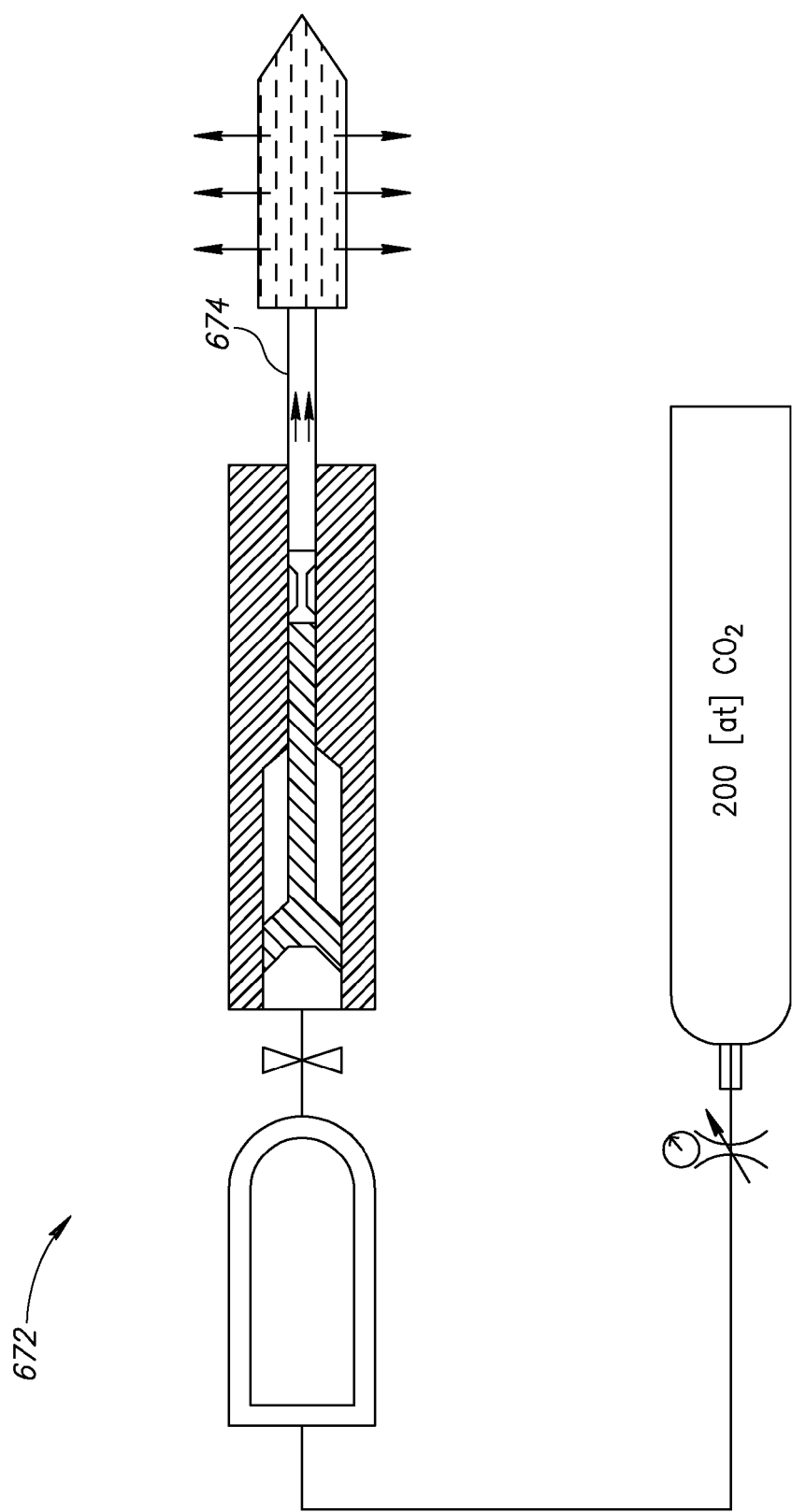

FIG. 6E is a schematic showing of a variant system 672 in which a filling 674 of the balloon is used instead of hydraulic fluid 658. Filling 674 may be provided ahead of time, for example, at manufacture. Optionally, any added drug is provided by injection into the balloon.

Figure 6F:
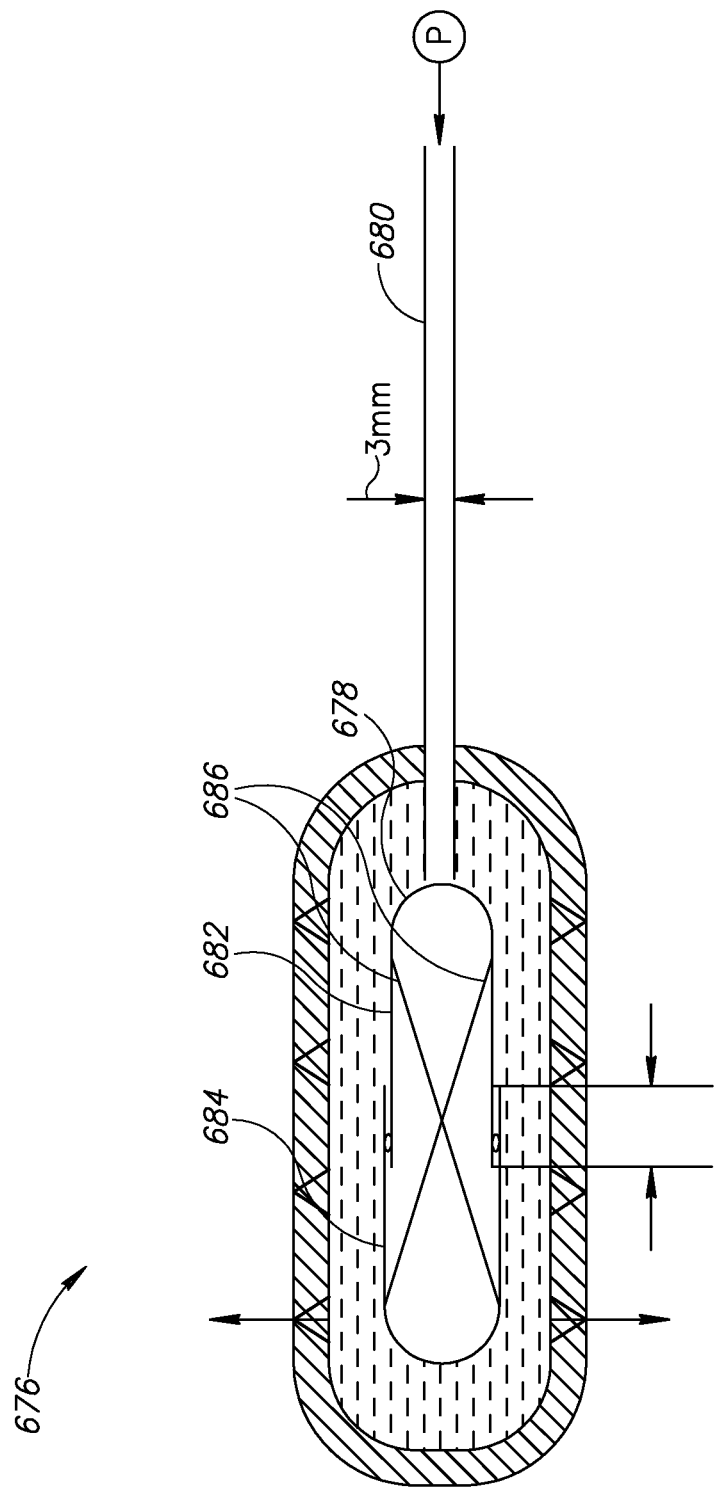

FIG. 6F is a schematic showing of a system 676, in which a two capsule 678 tears apart and thereby causes a pressure wave. In an exemplary embodiment of the invention, pressure is provided to the capsule via a lumen 680. Capsule 678 is provided in two parts, 682 and 684, which are coupled by a sliding seal and maintained together by one or more tension elements 686, for example, wires. As the pressure is increased, the tension on the wires increases until they fail, releasing the capsule parts. Optionally, the pressure applied by the capsule can be determined by calculating the failing point of the wire and the cross-section of the capsule.

Figure 6G:
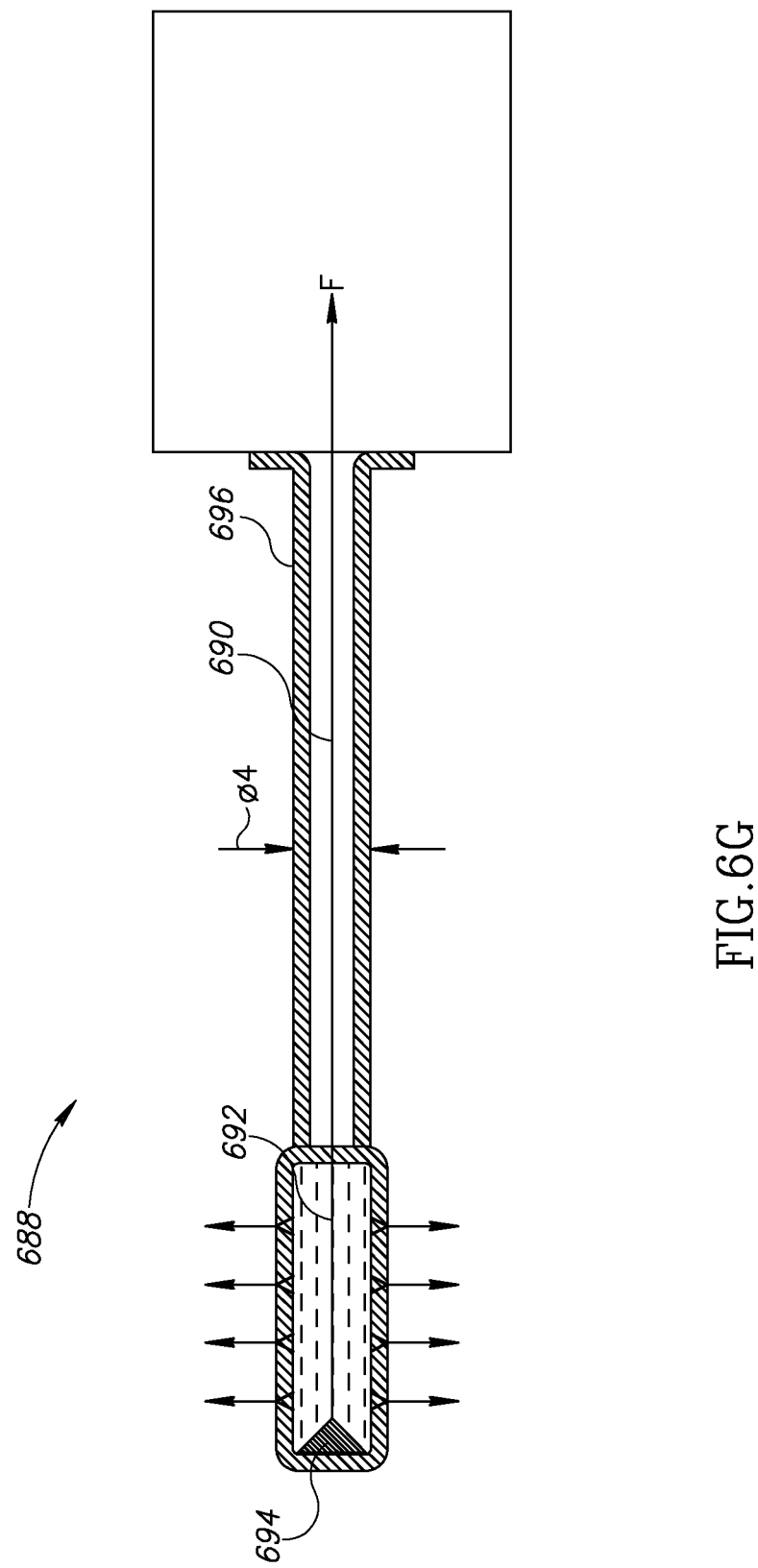

FIG. 6G shows a system 688, in which a wire 690 is pulled back to deliver a pressure impulse in a balloon 692. In an exemplary embodiment of the invention, a plunger 694 is attached to the distal end of wire 690 and fits inside balloon 692, such that pulling back will force fluid movement before plunger 694. Optionally, the catheter has a rigid body 696 (e.g., for use in a prostate). Alternatively, a braided body or other design that resists kinking upon axial compression is used. Optionally, the inflation of the balloon serves to reduce or prevent movement of the balloon during pullback of the wire (or other forces such as applied in other embodiments).

Figure 6H:
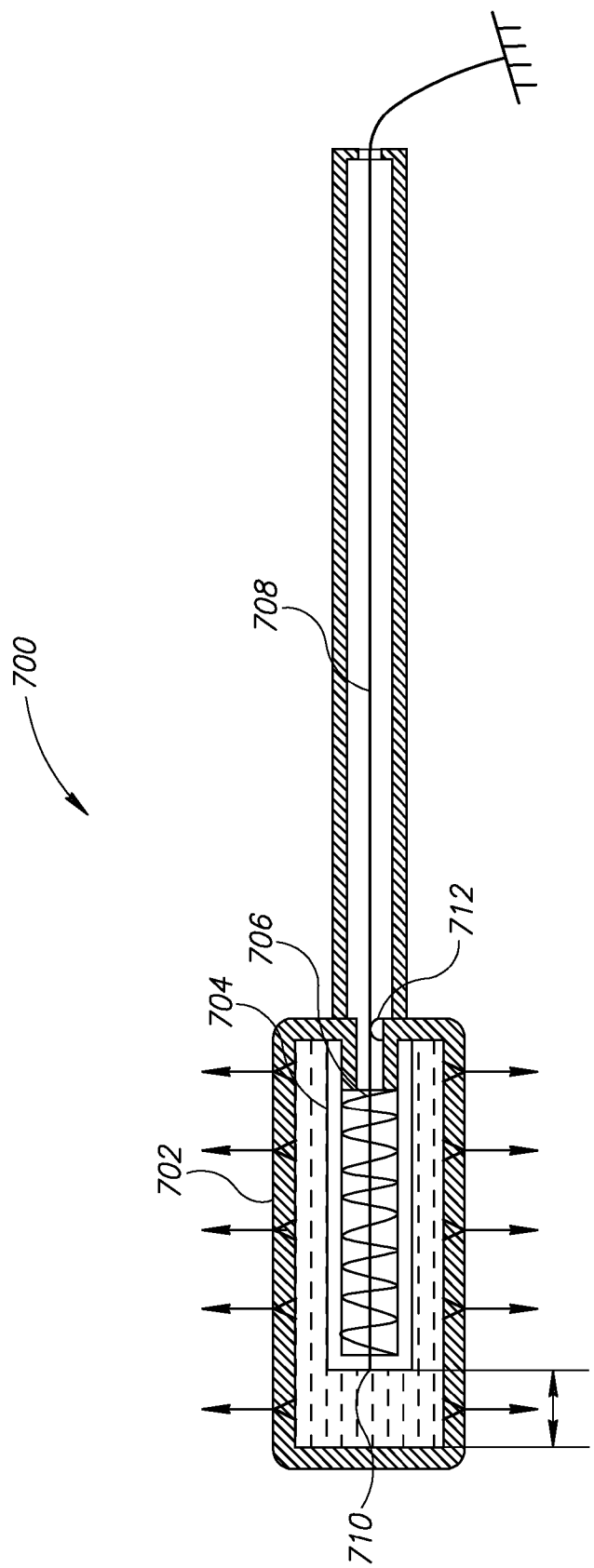

FIG. 6H shows a system 700, in which a capsule 704 is provided inside a balloon 702 and a spring 706 is positioned to selectively expand capsule 704. However, a tension element 708, such as a wire, prevents such extension. When wire 708 is released or cut, the spring can expand the capsule and create a pressure pulse. Optionally, wire 708 is attached to capsule 704 at a point 710, which is selectively releasable. In one example, point 710 burns or melts upon application of an electric field to wire 708 (or a light pulse to an optical fiber tension element). Optionally, wire 708 is attached as well at a point 712 to capsule 704, such that tension in wire 708 is mainly between points 710 and 712 and inside the balloon element and not along the entire catheter.

In this and other embodiments, the balloon can be pre-filled with the material to be injected.

Figure 7:
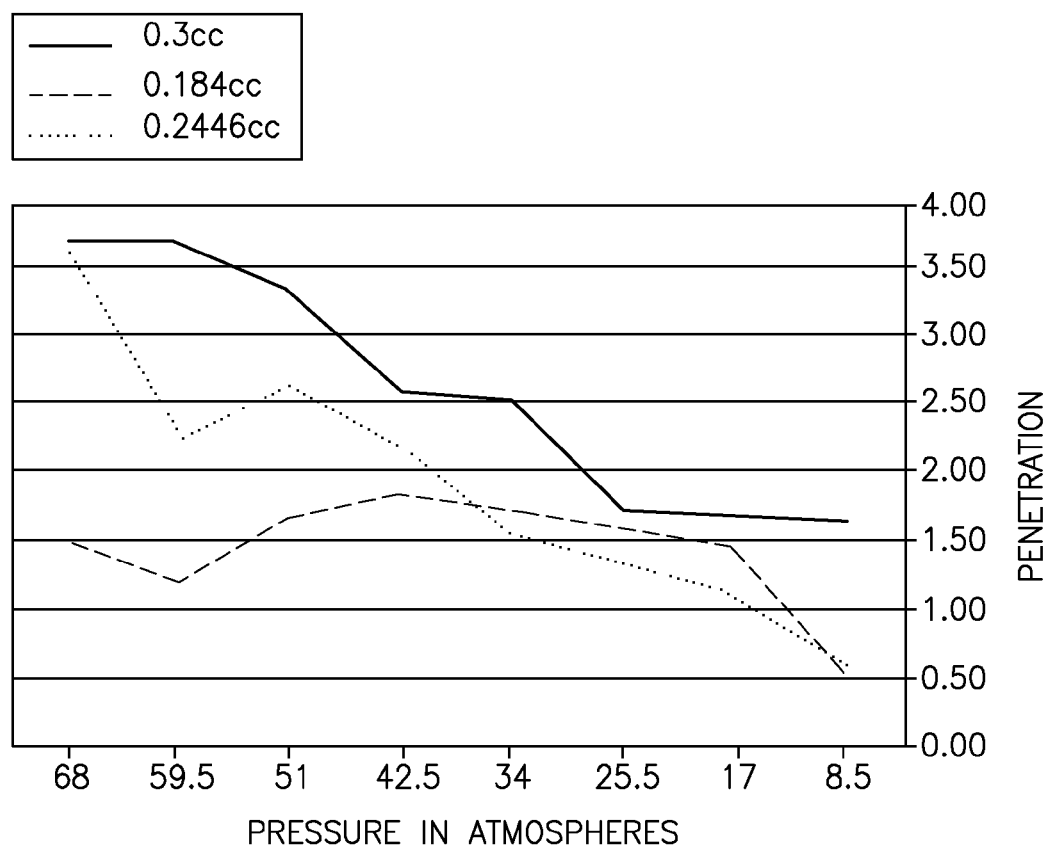
FIG. 7 is a graph summarizing experimental results showing penetration depth as a function of pressure and amount of delivery material.

FIG. 7 is a graph showing penetration depth of a dye into a bovine aorta under various conditions. The injection system was a gas powered system that applied up to 68 atmospheres to a piston attached to a tube 4 mm in diameter and 250 mm in length. The tube is attached to a hollow tube section with a diameter of 9.6 mm and 120 radial holes with a diameter of 50 microns and inter-hole spacing of about 2 mm. The system provides an amplification of pressure of a factor of 8.

In the graph, the solid line indicates the penetration depth in mm as a function of the applied pressure, for a 0.3cc bolus. The large dashes are for a case of 0.184 cc and the small dashes for 0.2446 cc. As can be seen, increasing pressure increases penetration depth. Size of bolus also appears to increase the penetration depth. Each point on the graph is an average of several (e.g., 4) experiments. The aorta was firmly attached to the ejection holes, probably with a contact pressure below 2 atmospheres.

Figure 8:
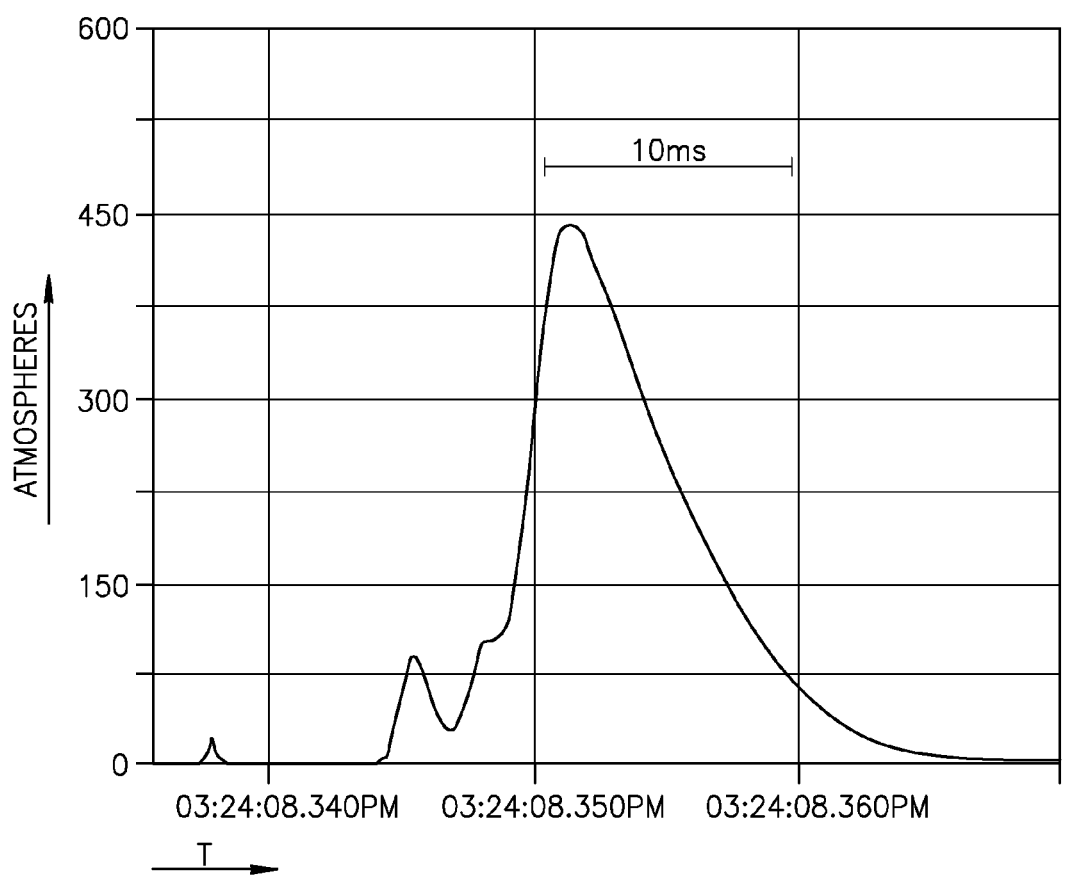
FIG. 8 is a graph showing a pressure waveform measured inside a delivery system in accordance with an exemplary embodiment of the invention.

FIG. 8 is a graph showing the peak pressure as measured in the hollow tube section as a function of time for a 68 atmosphere pulse (e.g., amplified by a factor of 8 during delivery). The pulse ended when all the material was ejected from the hollow tube. The mean velocity of the jet is estimated to be 60 m/s. It is believed that penetration depth is affected by one or both of mean velocity and peak velocity. In an exemplary embodiment of the invention, other mean and/or peak velocities can be achieved, for example, 10 m/s, 40 m/s, 100 m/s, 200 m/s, 300 m/s or smaller, intermediate or larger speeds. If a sufficiently large pressure is applied, very high peak velocities can be achieved, for example, 1000 m/s, 1500 m/s or faster, such as above the speed of sound in tissue (e.g., using shock waves).

Additional Applications

The above-described system and method may be used, for example, for coronary vessels and cerebral vessels.

The system and/or method, optionally with some variations (e.g., balloon diameter and/or flexibility, volume of injected material) may be adapted for other tubular organs in the body, for example, the gall bladder duct, the urethra, the ureters, the esophagus, air passage ways in the lungs, such as the bronchi and various peripheral blood vessels. It should be noted that in some of these embodiments, the above apparatus and/or methods are used to apply treatment without making a structural change and/or implanting a stent in the vessel being treated.

Illustrative examples are provided in some detail to demonstrate the scope and flexibility of the invention. These examples should not be construed to limit the invention, either singly or collectively.

Treatment of Atrial Fibrillation

In an exemplary embodiment of the invention, (FIG. 9A) a balloon 212 according to the present invention is deployed through a cardiac auricle 900 into vessel 200, optionally a pulmonary vein, to treat atrial fibrillation. In an exemplary embodiment of the invention, a cytotoxic substance is ejected radially or transaxially outwards from balloon 212 (arrows) to contact cells lining pulmonary vein 200. Optionally, the cytotoxic substance causes ablation and/or reduces a metabolic activity and/or alters an electrical property of cells lining the pulmonary vein. The ablated tissue blocks transmission of an electrical signal, such as an electrical signal causing Atrial Fibrillation. In an exemplary embodiment of the invention, an alcohol, such as ethanol, serves as a cytotoxic agent. A flow through balloon may optionally be employed to permit uninterrupted blood flow through pulmonary vein 200.

Figure 9A:
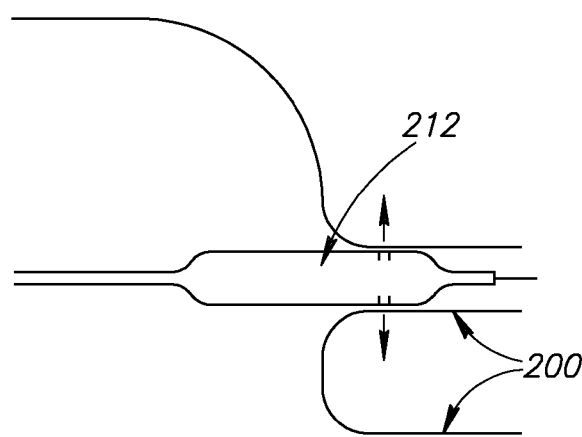
FIGS. 9A and 9B and 9C illustrate additional exemplary embodiments of the invention.
Figure 9A:
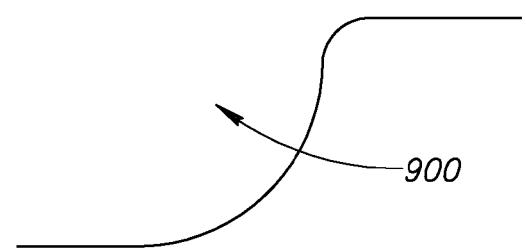
Figure 9B:
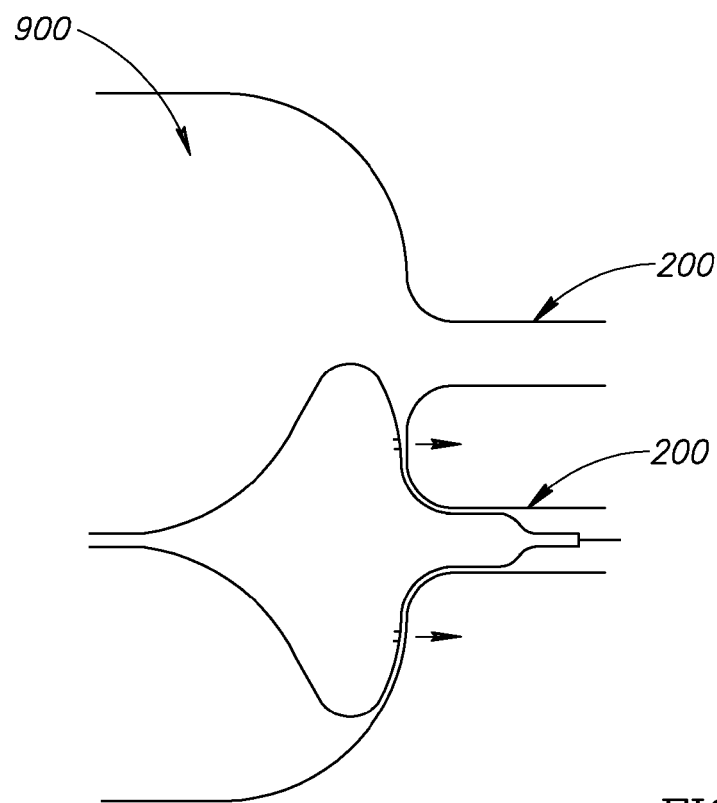

Various atrial fibrillation embodiments of the invention employ balloons of different physical configurations. For example, a balloon shape which helps align the balloon in the pulmonary vein may be employed (FIGS. 9A and/or 9B). Optionally, the balloon will have a "flow through" design so that blood flow is not interrupted. In some exemplary embodiments, injection into tissue is radial with respect to the balloon (FIG. 9A). In some exemplary embodiments, injection has an axial component with respect to the balloon but injects in a ring shaped pattern on a tissue surface surrounding the pulmonary vessel 200 (FIG. 9B).

Use in the Digestive Tract

Delivery of a cytotoxic substance to a selected area or areas in the intestine as described above could be used to block digestion of food, either temporarily or permanently. In order to permanently block food digestion, an amount of cytotoxic substance delivered to the intestine must be sufficient to kill progenitor cells responsible for replenishing cells lining the intestinal lumen. In an exemplary embodiment of the invention, this technique offers an alternative to intestinal resection in the treatment of obesity. Alternatively or additionally, using an agent which causes only temporary blocking of digestion can serve as a means of screening obese patients to identify those that are likely to benefit from intestinal resection.

Alternatively or additionally, a balloon according to the present invention may be employed to deliver a cytotoxic and/or chemotherapeutic agent to a tumor located in the digestive tract. The tumor may be located, for example, on an inner surface of a digestive organ such as the stomach, small intestine or large intestine. Alternatively or additionally, pancreatic tumors may be treated by deploying a balloon according to the present invention through the intestinal tract via the gall bladder to the pancreas.

Balloons for use in the GI tract may have different physical configurations depending upon their intended function. For example, a balloon to deliver cytotoxic substances to the intestine to prevent digestion would employ apertures spaced radially and axially along balloon with a length corresponding to the length of intestine to be treated. Alternatively or additionally, a balloon to deliver cytotoxic substances to a tumor located on the intestinal wall has apertures positioned along a side of a balloon positioned proximal to the tumor to be treated.

Treatment of the Urinary Tract

In an exemplary embodiment of the invention, a tumor, or group of tumors, on an inner surface of a urinary bladder is treated with a balloon according to the present invention. Treatment by direct injection of material into the tumor according to the present invention permits delivery of a higher concentration of a chemotherapeutic agent than would typically be achieved using previously available alternatives (e.g. "washing" the urinary bladder with the chemotherapeutic agent). Alternatively or additionally, direct injection of material into the tumor according to the present invention reduces a cytotoxic effect of the treatment on non-tumor cells lining the urinary bladder and/or a systemic cytotoxic effect.

Figure 9C:
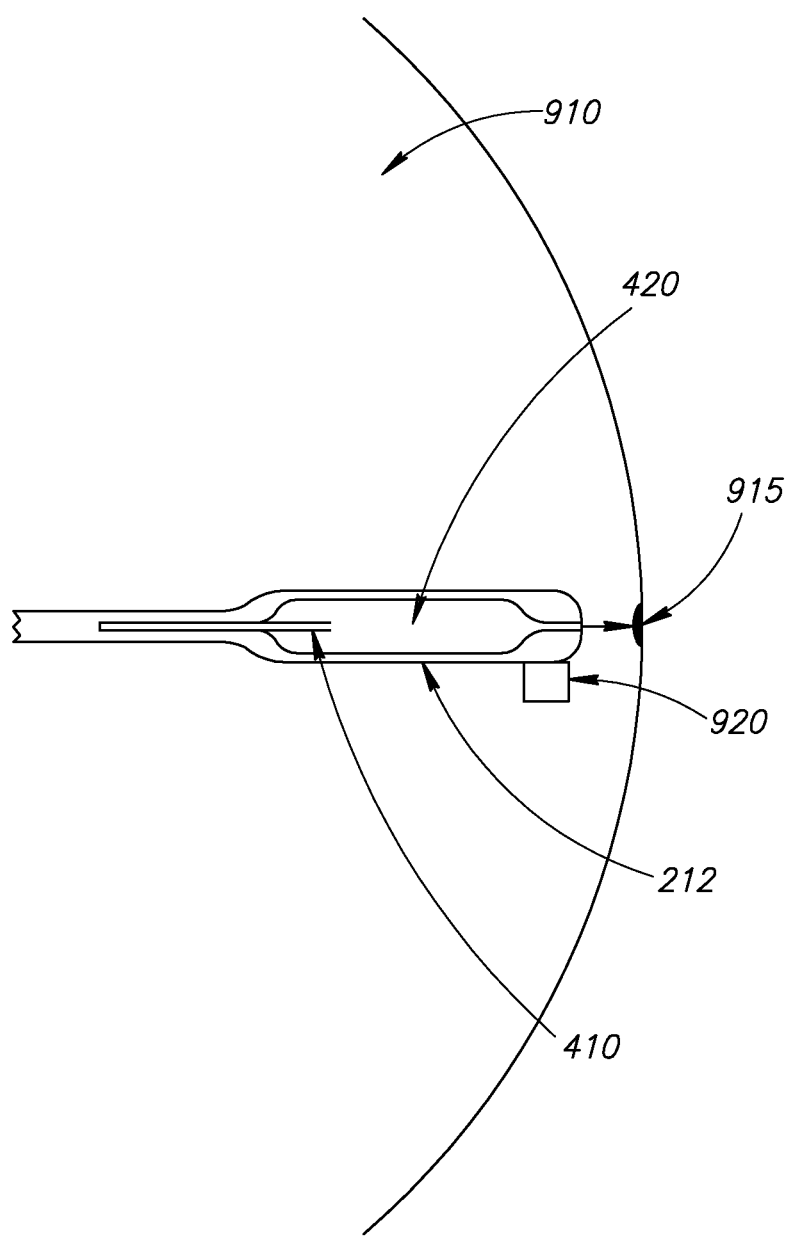

FIG. 9C illustrates a balloon 212 according to the present invention deployed through a lumen of a urinary bladder 910. Optionally, a camera 920 is provided to permit positioning of balloon 212 in proximity to a tumor 915 growing on an inner wall of bladder lumen. Inflation of balloon 212 is not necessarily required for positioning. In an exemplary embodiment of the invention, a cytotoxic agent is ejected outwards from balloon 212 (arrows) and injected into tumor 915. The cytotoxic agent may optionally be a chemotherapeutic such as, for example, BCG. Injection may optionally be axial as pictured. Use of balloons according to the invention permits a high concentration of a therapeutic agent to be applied directly to tumor 915. Alternatively or additionally, direct injection using a balloon, limits dispersal of the applied agent throughout the volume of bladder 910. The high concentration may be, for example, 1, optionally 10, optionally 25, optionally 50, optionally 75, optionally 100 nanograms per milligram of target tissue or lesser or intermediate or greater values.

In an exemplary embodiment of the invention, a balloon 212 with a large surface containing injection ports (as in FIG. 9B) delivers a chemotherapeutic agent to a large area. This exemplary configuration may be employed, for example, to inject axially into an inner wall surface of a urinary bladder 900. In the pictured embodiment, the tumors (not shown) are grouped around ureter 200. Optionally, a portion of balloon 212 protrudes into ureter 200 to correctly position the balloon. Optionally, this eliminates the need for a camera to assist in positioning.

Treatment of Tumors in Other Lumens

The methodology described in conjunction with FIG. 9C is generally applicable to cancer treatment at other body lumens. In an exemplary embodiment of the invention, a balloon 212 is deployed in any body lumen to deliver a therapeutic agent to a tumor from outside the tumor.

The invention has clinical utility in, for example, treatment of oral, nasal, pharyngeal, lung, esophageal, gastric, intestinal, colonic, pancreatic, rectal, cervical, uterine and prostate cancer. Optionally, balloon 212 may be mounted on an endoscope, for example a colonoscope, to aid in directing it to a desired location.

Intratumor Chemotherapy

In an additional exemplary embodiment of the invention, a balloon 212 is guided to a position within a tumor to deliver a therapeutic agent to a tumor from within the tumor. Optionally, guiding is through a blood vessel. Optionally, the balloon is guided through a capsule wall. In an exemplary embodiment of the invention, a guidewire tip and/or a guiding catheter make a hole in the capsule wall and a balloon according to the invention is guided through the hole. In the context of cancer treatment, the therapeutic agent may be, for example, a chemotherapeutic agent, a sclerosing agent, a gene therapy agent, an anti-angiogenic agent, an antibody or any other agent deemed useful in tumor treatment. In an exemplary embodiment of the invention, balloon 212 is employed to deliver therapeutic agents to tumors either on surfaces or inside organs.

In an exemplary embodiment of the invention, a balloon according to the invention is inserted directly into a tumor via a channel created specifically to facilitate insertion of the balloon. The channel may be created, for example, by insertion of a guidewire, cannula or stylet.

Dermatologic Applications

In an exemplary embodiment of the invention, a balloon 212 may be employed to deliver a therapeutic agent intradermally to cells of a relatively large skin surface. For applications of this type, balloon 212 may be configured to have a substantially flat or slightly curved aspect (as in FIG. 9B and/or 9C) so that it conforms to a skin surface to be treated in size and/or shape. Optionally, a balloon constructed for dermatologic applications will be stiff or flexible at the portion destined to be positioned near or contact the skin. In an exemplary embodiment of the invention, the balloon is filled with a therapeutic agent at a pressure in the range of 1 atmosphere. Optionally air is removed from the balloon. In an exemplary embodiment of the invention, delivery of the therapeutic agent into the skin is driven by an energy pulse which produces a pressure of 10, optionally 20, optionally 50, optionally 100, optionally 150, optionally 200 atmospheres or lesser or greater or intermediate values.

Optionally, this embodiment is useful in local treatment of a skin disease such as psoriasis, dermatitis or leprosy, acne, tinea, pityriasis and herpes zoster. Relevant therapeutic agents include, but are not limited to cortisone, calcipotriol, steroids and combines including one or more of these agents. In an exemplary embodiment of the invention, the balloon delivers cortisone and at least one additional hormone, optionally a steroid hormone.

Intradermal, as opposed to transdermal, injection relies upon dispersion or spreading of a small amount of a delivered agent over a relatively large skin surface and delivering the agent at a velocity which introduces the agent into the skin, but not through the skin. The present invention avoids the need for topical application or subcutaneous delivery. Previously available needleless injection devices typically provide an injection velocity of 100-500 m/s which causes injected material to pass through the skin. In an exemplary embodiment of the invention, the injection velocity for intradermal treatment is in the range of 10-50 m/s, optionally 10-40 m/s, optionally 10-25 m/s, optionally 10-15 m/s or lesser or intermediate or greater values. These lower velocities are sufficient to propel liquid droplets into the skin without causing penetration to subdermal tissue layers as a standard needleless injector does.

Transmucosal Applications

In an exemplary embodiment of the invention, a balloon according to the present invention is employed to inject medications through mucous membranes to underlying cells. Most skin surfaces are not covered by a mucosal layer unless they are within a body cavity (e.g. oral cavity). Optionally, injection of medications through mucous membranes permits treatment of any cell layer covered by a mucosal layer. Mucosal layers line, for example, the digestive tract, the genitourinary tract, the buccal cavity, the nostrils, the oral cavity and the nasal sinuses.

Mucosal layers exist to protect underlying cells. Previously available alternatives typically permitted delivery of therapeutic agents onto a mucosal layer, but not through the mucosal layer. Because mucosal layers in general are characterized by a high turnover rate and/or a high non-specific binding capacity, delivery of a therapeutic agent onto the mucosal layer using prior art technology often effectively reduced the amount of agent delivered to a desired target. Alternatively or additionally, mucosal secretions are frequently re-absorbed into the body (e.g. mucous secreted in the nasal sinuses may drip into the mouth where it is subsequently swallowed and digested). This re-absorption can lead to undesired systemic side effects of mucosally delivered drugs. For at least these reasons, prior art solutions for local delivery of therapeutic agents to a tissue covered by a mucosal layer were characterized by a low efficacy and/or high incidence of systemic side effects.

In an exemplary embodiment of the invention a balloon according to the invention is inserted into at least one nostril. Optionally, inflation causes the balloon to conform to at least a portion of a nostril and/or nasal sinus. Delivery of a therapeutic substance may, for example, ameliorate or relieve symptoms of rhinitis (e.g. allergic rhinitis or rhinitis caused by infection) and/or sinusitis and/or upper respiratory tract infections.

Useful therapeutic agents in this context include, but are not limited to antihistamines, decongestants, steroids and antibiotics. Alternatively or additionally, a sclerosant agent may be employed. Sclerosants may act by shrinking an inferior turbinate and/or other hypertrophic nasal tissue(s). Optionally, the shrinking of hypertrophic tissue relieves nasal obstruction.

Previously available topical delivery devices for the nose and/or sinuses delivered therapeutic agents at low pressures (e.g. spay bottle, metered dose inhaler, nebulizer and vaporizer). The low pressure delivery generally did not cause the delivered agent(s) to pass through the mucous membranes into underlying cells. Because of the high turnover of mucous, especially in acute rhinitis, much of the active ingredient(s) was not absorbed by target cells using these delivery methods.

Previously available systemic treatment modalities required large amounts of medication to reach an effective local (e.g. intranasal) concentration. The large amounts of medication required for systemic treatment often caused undesirable systemic side effects.

Optionally, a catheter may be employed to guide a balloon 212 deeply into a mucosally lined lumen. This may be useful, for example, in treatment of chronically infected nasal sinuses or uterine inflammation and/or infection and/or tumors.

In an additional exemplary embodiment of the invention a balloon is inserted into a stomach or duodenum to treat gastric or duodenal ulcers. Useful therapeutic agents in this context include, but are not limited to, acid reducers and antibiotics.

In an additional exemplary embodiment of the invention a balloon is inserted into an intestine to treat an inflammatory bowel disease (e.g. Ulcerative colitis or Crohn's disease). Useful therapeutic agents in this context include, but are not limited to, anti-inflammatory drugs (e.g. steroids and/or non-steroid anti-inflammatory drugs [NSAIDS]) and immunosuppressive drugs.

Buccal Cavity Treatment

In an exemplary embodiment of the invention, a balloon according to the invention is employed to deliver a therapeutic agent to the soft palate. Optionally, the therapeutic agent is useful in reducing snoring and/or obstructive sleep apnea. Optionally, the therapeutic agent is a sclerosant. Sclerosants can increase formation of connective tissues such as collagen by inducing fibrosis. Optionally, stiffening of the soft palate is achieved. Injection can be applied on the surface or by introduction of a catheter.

In an exemplary embodiment of the invention, a balloon 212 delivers a therapeutic agent to the tonsils and/or adenoids. Optionally, the therapeutic agent is useful in reducing swelling and/or has antibiotic properties. Optionally, the therapeutic agent is a sclerosant. In an exemplary embodiment of the invention, treatment with a balloon 212 obviates a need for surgical intervention.

In an exemplary embodiment of the invention, a balloon according to the invention injects a therapeutic agent into the tonsils and/or adenoids and/or soft palate and/or inferior nasal turbinates. Relevant therapeutic agents in this context include glues, sclerosants, antihistamines, decongestants, corticosteroids and antibiotics In an exemplary embodiment of the invention, the therapeutic agent includes a glue which makes the tissue stiffer. Optionally stiffening and/or shrinking caused by the therapeutic agent reduces vibration. Optionally, a decrease in vibration ameliorates snoring.

Scar Therapy

In an exemplary embodiment of the invention, a balloon 212 delivers a therapeutic agent which mitigates scarring. Optionally, the scars to be treated resulted from granulation and/or tumor growth. Optionally, treatment of scar tissue in the trachea and/or esophagus is undertaken. Optionally, the therapeutic agent includes a scar modifying medication. Optionally, the scar modifying medication includes a steroid hormone and/or mithomycin C and/or immuno-suppressant drug. In an exemplary embodiment of the invention, treatment of airway stenosis or stenosis of the digestive tract is achieved. Optionally, symptoms of cystic fibrosis and/or Autoimmune diseases such as: myasthenia gravis and/or Graves' disease and/or Rheumatoid arthritis and/or Necrotic vasculitis and/or System lupus erythematodis and/or Scleroderma with pulmonary fibrosis are ameliorated and/or relieved. In an exemplary embodiment of the invention, delivery is to tissue surrounding the scar and/or to the scar itself.

Gene Therapy

In an exemplary embodiment of the invention, a balloon with injection ports delivers a medicament containing microparticles and/or nanoparticles. Optionally, the medicament contains a gene therapy reagent. In an exemplary embodiment of the invention, the balloon facilitates somatic cell gene therapy by injecting a nucleic acid vector into a target tissue.

Other Considerations

Optionally, the system and method are used to deliver a material to only one side of the balloon. Exemplary applications include the larynx, pharynx, vocal cords, voice box and/or base of tongue.

Optionally, the system and/or method are used for cosmetic applications, for example for stiffening tissue by injecting structural material into the tissue, for example, using a catheter (optionally without a balloon) inserted under the skin.

In an exemplary embodiment of the invention, injection of structural material is used for strengthening an anastomosis region, for example, to help support vessels damaged by the manipulation and/or tensions associated with anastomosis. Optionally, injection of a structural material does not prevent further growing in diameter of the treated vessel. This may be useful, for example, when the treated vessel is a small vessel which may grow (e.g., to respond to additional demand), or when treating children. Optionally, changes in diameter allow the vessel to respond to pulse waves and/or changes in blood pressure.

The following PCT publications, the disclosures of which are incorporated herein by reference, describes methods for anastomosis and hole closure which may be used together with injection of materials into the treated region, for example, to reduce the volume of a connector used or to structurally stabilize diseased tissue: WO 99/62408, WO 99/62415, WO 00/56226, WO 00/56223, WO 00/56227, WO 00/56228, WO 01/4162, WO 01/41624, WO 01/70091, WO 01/70118, WO 01/70119, WO 01/70090, WO 02/47561, WO 02/30172, WO 02/47532, WO 02/074188, WO 03/026475, WO 2004/028377, WO 2004/028380, WO 2004/028376, WO 2005/027750, WO 2004/028378, WO 2004/043216, WO 2005/013836, WO 2005/055801. The disclosures of all of these documents are incorporated herein by reference.

In an exemplary embodiment of the invention, injection of glue or other structural material is used to aid attachment to a wall of a blood vessel. In one example, glue is injected into a wall to strengthen it so that it may be used for attaching an anastomosis connector thereto. In an exemplary embodiment of the invention, a calcified aorta is treated, to prevent breakaway of material during anastomosis or bypass procedures. In an exemplary embodiment of the invention, the injection is used to attach small hooks or stubs (e.g., of the glue material) to the wall, on which stubs a patch or a connector or other vessel may be attached. Optionally, the stubs are created by the apertures including an offset, for example 0.5-1 mm. Optionally, the stubs are created by injection using a needle and pulling back the needle slowly.

In an exemplary embodiment of the invention, while injection using needleless methods are described, needle based methods may be used, especially for structural materials such as glue. Optionally, a plurality of needles are provided on the outside of the balloon. Alternatively or additionally, the needles are provided on tubes 644 and 646. Alternatively or additionally, the needles are provided on a balloon or other expandable structure inside of balloon 642 and then, when deployed, the needles extend through the wall of balloon 642 (or other balloon design) and penetrate the nearby vessel walls. In an exemplary embodiment of the invention, the needles are 1 mm or less in length and/or diameter, for example, less than 0.5 mm. Optionally, 5, 10, 20 or an intermediate or larger number of needles are provided.

In a prostate application, the balloon (e.g., 642) is optionally made more or completely rigid, for example, being a metallic balloon. This may be useful for prostate treatments. Optionally, the rigid balloon does not expand, and is more properly termed a hollow element. Alternatively, the balloon expands but is non-compliant.

While the above embodiments have focused on radial ejection of material, optionally, axial ejection is provided. In an exemplary embodiment of the invention, a balloon employed for forward injecting of material holds the ejection port in a stable orientation and may help prevent misses of the target and/or motion of the ejection port due to the third law of motion. Optionally, forward ejection is used to help dissolve thrombosis, for example, by assisting in the distribution of material into the thrombosis.

Physical Configuration of the Balloon

The above description has focused on in-vivo treatment especially of blood vessels and that focus has led to use of the term "tube" and other geometrical shapes which have been described and used for generality. However, methods and/or apparatuses described herein are suitable for use in treatment of other tissue and/or treatment outside the body so that various embodiments of the invention include physical configurations adapted for the intended use.

In an exemplary embodiment of the invention, the balloon used will have a non tubular geometry. Optionally, a balloon according to the invention will be characterized by at least one flat side. Optionally, a balloon according to the invention will be in the form of a polygonal solid such as, for example, a cylinder, a cone, a pyramid or a cube.

In an exemplary embodiment of the invention, a tube need not have a full body nor have a circular cross-section. Alternatively or additionally, balloon 212 may optionally be fashioned so that it forms an inner flow through channel when inflated. A flow through channel may be created, for example by fashioning balloon 212 as a toroid ring or hollow cylinder. This type of design may be advantageous, for example, when treating a major blood vessel, such as the aorta or a carotid artery. The flow through channel prevents ischemia when the balloon is inflated in the blood vessel.

Optionally, balloons according to the invention may be sized for specific applications. For example, a balloon for coronary applications might have a diameter of 2 to 3.5 mm and a length of 10 to 25 mm. A balloon intended for deployment in the prostate might be considerably larger, for example a diameter of 6 to 11 mm and a length of 20 to 40 mm.

Alternatively or additionally, particular modifications may be desired for certain vessel types. For example, the aorta is thicker, while a coronary vessel is thinner, thus suggesting different ejection parameters, powers and/or balloon pressures and sizes. For example, an aorta may be 3 mm thick, while a coronary vessel may be less than 1 mm thick.

Measurements are provided to serve only as exemplary measurements for particular cases. The exact measurements stated in the text may vary depending on the application, the type of vessel (e.g., artery, vein, xenograft, synthetic graft), shape of plaque (e.g., local, elongate, thin, thick, outer remolding, vulnerable) and/or sizes of vessels involved (e.g., 1 mm, 2 mm, 3 mm, 5 mm, aorta sized).

It will be appreciated that the above described methods of material injection may be varied in many ways, including, changing the order of steps and the types of tools used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features, also for different embodiments, are also considered to be within the scope of some embodiments of the invention. Also within the scope of the invention are surgical kits which include sets of medical devices suitable for performing, for example, a single or a small number of tissue treatments. In some embodiments, one or more of the devices, generally sterile, described above, are packaged and/or sold with an instruction leaflet and/or portions of treatment materials, describing the device dimensions and/or situations for which the device should be applied and/or what materials should be used. With regard to the controller, various implementations are considered within the scope of the invention, including hardware, firmware software, computers loaded with suitable software and/or computer readable media having software thereon suitable for supporting the methods described herein. Section headings where they are provided are intended for aiding navigation and should not be construed to limiting the description to the headings. When used in the following claims, the terms "comprises", "includes", "have" and their conjugates mean "including but not limited to".

It will be appreciated by a person skilled in the art that the present invention is not limited by what has thus far been described. Rather, the scope of the present invention is limited only by the following claims.

What is claimed is:

1. A method for injecting a therapeutic agent into a target tissue, the method comprising:
   (a) providing an expandable member including an outer wall characterized by a plurality of exit sites therein, said outer wall defining an inner cavity;
   (b) filling the inner cavity with a flowing therapeutic agent to a defined first pressure sufficient for performance of PTCA;
   (c) thereafter, increasing said pressure to a second pressure in excess of said defined first pressure to open said exit sites; and
   (d) releasing the therapeutic agent through the exit sites, said second pressure being such that one or more jets are formed when the therapeutic agent is released through said open exit sites,
   (e) wherein the velocity of the released therapeutic agent is sufficient for the therapeutic agent to penetrate the target tissue.

2. A method according to claim 1, wherein said expandable member includes at least one balloon.

3. The method according to claim 1 wherein the second pressure is 16 ATM.

4. The method according to claim 1 wherein the second pressure is 20 ATM.

5. A method according to claim 1, where the second pressure is at least 15 atmospheres.

6. A method according to claim 1, where the second pressure is sufficient to cause said therapeutic agent to exit through said apertures at a speed of at least 20 meters/second.

7. A method according to claim 1, wherein the therapeutic agent enters the target tissue intracellularly.

8. A method according to claim 1, wherein the target tissue is located around a body lumen.

9. A method according to claim 1, wherein at least some of said exit sites are aimed transaxially with respect to said expandable member.

10. A method according to claim 1, wherein at least some of said exit sites are aimed radially with respect to said expandable member.

11. The method according to claim 1, further including performing PTCA at said defined first pressure before increasing the pressure to said second pressure.

12. A method according to claim 8, wherein said body lumen is a blood vessel.

13. A method according to claim 1, wherein the therapeutic agent includes a cytotoxic agent.

14. A method according to claim 1, wherein the therapeutic agent includes a fibrotic agent.

15. A method according to claim 13, wherein said cytotoxic agent includes an alcohol.

16. A method according to claim 15, wherein said alcohol includes ethanol.

17. A method according to claim 13, wherein entry of said cytotoxic agent into said target tissue blocks transmission of an electric signal through said target tissue.

18. A method according to claim 17, applied to ameliorate Atrial Fibrillation.

19. A method according to claim 1, wherein the therapeutic agent includes a chemotherapeutic agent.

20. A method according to claim 1, wherein the target tissue is a tumor.

21. A method according to claim 20, wherein the tumor is located on an inner surface of a urinary bladder.

22. A method according to claim 1, wherein the therapeutic agent includes an anti-proliferation compound.

23. The method according to claim 1, wherein the expandable member includes an inner expandable member and an outer expandable member and wherein the exit sites are formed from a plurality of apertures on the outer expandable member sealed by the inner expandable member.

24. The method according to claim 23, wherein the therapeutic agent is released by rupture of the inner expandable member to expose at least one exit site.

25. A method according to claim 1, further including positioning the expandable member using an image guidance system.

26. A method according to claim 11, further including positioning the expandable member using an intrabody camera.

27. A method according to claim 1, wherein said target tissue includes a portion of a pulmonary vein conducting an electric signal which contributes to Atrial Fibrillation.

28. A method according to claim 1, wherein said therapeutic agent enters said target tissue at a concentration of at least 1 nanogram per milligram of tissue.

29. A method according to claim 1, wherein said therapeutic agent includes particles with a size in the range of 1 nanometer to 100 micrometers.

30. A method according to claim 29, wherein said particles include at least one metal.

31. A method according to claim 29, wherein said particles include at least one nucleic acid sequence.

32. A method according to claim 1, wherein said body cavity includes a nostril.

33. A method according to claim 1, wherein said body cavity includes a nasal sinus.

34. A method according to claim 1, wherein said body cavity includes a portion of a genitourinary tract.

35. A method according to claim 1, wherein said body cavity includes a portion of a digestive tract.

36. A method according to claim 1, wherein said body cavity is a nostril and/or adjoining nasal sinuses and the method provides relief from rhinitis.

37. A method for injecting a fluid to penetrate into a tissue, the method comprising:
  (a) expanding a member including an outer wall defining an inner cavity, and characterized by a plurality of exit sites therein;
  (b) filling said inner cavity with a flowing therapeutic agent at a defined first pressure sufficient for performance of PTCA without significant leakage through said exit sites; and
  (c) releasing said therapeutic agent by transforming said exit sites into ejection ports through which the therapeutic agent can exit by increasing the pressure to a second pressure above said desired pressure at said exit sites;
  (d) and delivering said therapeutic agent through said ejection ports at a velocity sufficient to penetrate adjacent tissue, wherein said therapeutic agent is delivered into said target tissue in such a manner that it exerts a physiologic effect on cells of said target tissue but does not exert a substantial effect on cells lying at a distance greater than a selected distance from said target tissue.

38. A method according to claim 1, wherein
said therapeutic agent is released through the exit sites at a velocity at which one or more jets are formed when the therapeutic agent is released through said exit sites; and which is sufficient for intradermal penetration of said jets, but insufficient to cause transdermal penetration.

* * * * *